US008513231B2

(12) United States Patent
Hubschwerlen et al.

(10) Patent No.: US 8,513,231 B2
(45) Date of Patent: *Aug. 20, 2013

(54) USE OF OXAZOLIDINONE-QUINOLINE HYBRID ANTIBIOTICS FOR THE TREATMENT OF ANTHRAX AND OTHER INFECTIONS

(75) Inventors: Christian Hubschwerlen, Durmenach (FR); Jean-Luc Specklin, Kembs-Schaeferhof (FR); Daniel Baeschlin, Arlesheim (CH); Hans Locher, Binningen (CN); Christine Schmitt, Kunheim (FR)

(73) Assignee: Morphochem Aktiengesellschaft fü Kombinatorische Chemie, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/596,700

(22) Filed: Aug. 28, 2012

(65) Prior Publication Data
US 2012/0322766 A1    Dec. 20, 2012

Related U.S. Application Data

(60) Continuation of application No. 12/987,611, filed on Jan. 10, 2011, now Pat. No. 8,268,812, which is a division of application No. 10/554,732, filed as application No. PCT/EP2004/003650 on Apr. 6, 2004, now abandoned.

(60) Provisional application No. 60/466,945, filed on Apr. 30, 2003, provisional application No. 60/530,822, filed on Dec. 18, 2003.

(51) Int. Cl.
*A61K 31/397* (2006.01)
*A61K 31/55* (2006.01)
*A61K 31/44* (2006.01)
*A61K 31/47* (2006.01)

(52) U.S. Cl.
USPC ............. 514/210.2; 514/217.07; 514/300; 514/312

(58) Field of Classification Search
USPC ............ 514/210.2, 217.07, 300, 312
See application file for complete search history.

(56) References Cited

U.S. PATENT DOCUMENTS

| | | | |
|---|---|---|---|
| 4,840,956 A | 6/1989 | Domagala et al. | |
| 5,221,676 A | 6/1993 | Laborde et al. | |
| 5,491,139 A | 2/1996 | Demuth, Jr. et al. | |
| 5,599,791 A | 2/1997 | Tavecchia et al. | |
| 5,808,076 A | 9/1998 | Vetter et al. | |
| 5,861,413 A | 1/1999 | Habich et al. | |
| 5,998,436 A | 12/1999 | Yazaki et al. | |
| 6,239,152 B1 | 5/2001 | Gordeev et al. | |

| | | |
|---|---|---|
| 2004/0132764 A1 | 7/2004 | Locher |
| 2005/0096343 A1 | 5/2005 | Hubschwerlen et al. |
| 2007/0004769 A1 | 1/2007 | Hubschwerlen et al. |

FOREIGN PATENT DOCUMENTS

| | | |
|---|---|---|
| DE | 196 01 265 A1 | 7/1997 |
| EP | 0 266 576 A2 | 5/1988 |
| EP | 0 390 215 A2 | 10/1990 |
| HU | 224 072 B1 | 5/2005 |
| JP | 02069478 A | 3/1990 |
| JP | 2000-516239 A | 12/2000 |
| KR | 10 2000 00673606 | 11/2000 |
| KR | 2004-30712 Y1 | 11/2006 |
| RU | 2167873 C2 | 5/2001 |
| WO | 93/09103 A1 | 5/1993 |
| WO | 97/30995 A1 | 8/1997 |
| WO | 99/28317 A1 | 6/1999 |
| WO | 00/10566 A1 | 3/2000 |
| WO | 01/09107 A1 | 2/2001 |
| WO | 01/46164 A1 | 6/2001 |
| WO | 02/059116 A2 | 8/2002 |
| WO | 03/002560 A1 | 1/2003 |
| WO | 03/031441 A1 | 4/2003 |
| WO | 03/031443 A1 | 4/2003 |
| WO | 03/032962 A2 | 4/2003 |
| WO | 2004/069816 A1 | 8/2004 |
| WO | 2004/096221 A1 | 11/2004 |
| WO | 2005/023801 A1 | 3/2005 |
| WO | 2005/058888 A2 | 6/2005 |
| WO | 2007/017828 A2 | 2/2007 |
| WO | 2008/056335 A1 | 5/2008 |
| WO | 2008062379 A2 | 5/2008 |
| WO | 2009/136379 A1 | 11/2009 |

OTHER PUBLICATIONS

C. Hubschwerlen et al., "Design, Synthesis and Biological Evaluation of Oxazolidinone-Quinolone Hybrids", Bioorganic & Medicinal Chemistry, vol. 11, pp. 2313-2319 (2003).
C. Hubschwerlen et al., "Structure-Activity Relationship in the Oxazolidinone-Quinolone Hybrid Series: Influence of the Central Spacer on the Antibacterial Activity and the Mode of Action", Bioorganic & Medcinal Chemistry, vol. 13, pp. 4229-4233 (2003).
Locher et al., 42nd ICAAC (2002), poster and abstract F-1317—ICAAC 2002: San Diego, CA, Sep. 27-30, 2002).
C. Hubschwerlen et al., 43rd ICAAC, 2003, Chicago, IL, Sep. 14-17, 2003—Abstract F-2144.
F.Z. Dorwald et al., "Side Reactions in Organic Synthesis", 2005, wiley:VCH, Winheim p. IX of preface.
Patani et al., "Bioisosterism: A Rational Approach in Drug Design", Chem. Rev., 1996, pp. 3127-3176.
Hcaplus 138:338143: C. Hubschwerlen et al., "Preparation of dual action bactericides comprising a oxazolidinone and a quinolone or naphthyridinone moiety effective against multi-drug resistant bacteria", (2007).

(Continued)

*Primary Examiner* — Paul Zarek
(74) *Attorney, Agent, or Firm* — Edwards Wildman Palmer LLP; Peter F. Corless; Christine C. O'Day

(57) ABSTRACT

The present invention relates to the use of compounds, in which the pharmacophores of quinolone and oxazolidinone are chemically linked together through a linker that is stable under physiological conditions, for the treatment of anthrax and other infections.

15 Claims, No Drawings

(56) References Cited

OTHER PUBLICATIONS

Hcaplus 138:304289: C. Hubschwerlen et al., "Preparation of dual action bactericides comprising a oxazolidinone and a quinolone or naphthyridinone moiety effective against multi-drug resistant bacteria", (2007).

Hcaplus 138:304288: C. Hubschwerlen et al., "Preparation of dual action bactericides comprising a oxazolidinone and a quinolone or naphthyridinone moiety effective against multi-drug resistant bacteria", (2007).

Weidner-Wells et al., Bioorg. Med. Chem., 10(7), pp. 2345-2351 (2002).

Weidner-Wells et al., Bioorg. Med. Chem. Lett., 11(14), pp. 1829-1832 (2001).

R.B. Silverman, "The Organic Chemistry of Drug Design and Drug Action—2nd Edition", 2004, Elsevier Academic Press, pp. 29-32.

W.A. Gregory et al., "Antibacterials. Synthesis and Structure-Activity Studies of 3-Aryl-2-oxooxazolidines. 2. The "A" Group", J. Med. Chem., vol. 33, pp. 2569-2578 (1990).

A. Dalhoff, "A Report: Evaluation of the antibacterial activities of oxazolidinone-fluoroquinolone hybrids", (cited in the Grounds of Appeal of May 31, 2011 of European Patent 1 709 044).

Grounds of Appeal filed by Lederer & Keller in European Patent 1 709 044 (May 30, 2011).

H.H. Locher et al., "Synthesis and Antibacterial Action of Novel Quinolone-Linked Oxazolidinones", 42nd ICAAC, 2002, San Diego, CA, Sep. 27-30, 2002, Abstract F-1317.

C. Hubschwerlen et al., "New Oxazolinone-Quinolone Hybrids: Synthesis and SAR", 43rd ICAAC, 2003, Chicago, IL, Sep. 14-17, 2003, Poster F-2144.

H.H. Locher et al., "Antibacterial Characterization and Mode of Action of New Oxazolidinone-Quinolone Hybrids", 43rd ICAAC, 2003, Chicago, IL, Sep. 14-17, 2003, poster F-2145.

C. Gray et al., "Characterization of MCB 3681, a Dual-action Antibiotic", 45th ICAAC, 2005, Washington, DC, Dec. 16-19, 2005, poster F-512.

C. Gray et al., "Efficacy Studies of MCB 3837, a Dual-action Antibiotic, in Experimental Infections in Mice", 45th ICAAC, 2005, Washington, DC, Dec. 16-19, 2005, Poster F-513.

S. Schubert et al., "Low Propensity to Develop Resistance to the Novel Antibacterial MCB3681", 46th ICAAC, 2006, San Francisco, CA, Sep. 27-30, 2006, abstract F1-1968.

M. Kresken et al., "In vitro Activity of the Novel Antibacterial MCB3681 Against Selected Gram-Positive and -Negative Bacteria Compared to Established Antibiotics", 46th ICAAC, 2006, San Francisco, CA, Sep. 27-30, 2006, poster F1-1967.

Rompp Chemie Lexikon, 9 auglage, pp. 1892-1893 (1995).

A. Dalhoff et al., "Symposium: Multiple Mode of Action Antibiotics—The Quinolone-Plus Approach", ICAAC 2007, Sep. 17-20, 2007—Chicago.

W.A. Petrie et al., "Chapter 44—Antimicrobial Agents Sulfonamides, TrimethoprimSulfamethoxazole, Quinolones, and Agents for Urinary Tract Infections", Goodman & silman's The Pharmacological Basis of Therapeutics, 10th ed., Hardman JG, Limbird LE, and Gilman AG, Eds., McGraw-Hill, 2001, pp. 1171-1188.

S.R. Vippagunta et al., "Crystalline Solids", Advanced Drug Delivery Reviews, 48(1), pp. 3-26 (2001).

Centers for Disease Control and Prevention, "Anthrax: What You Need to Know", http://www.bt.cdc.gov/agent/anthrax/needtoknow.asap, last updated Jul. 2003.

F.A. Carey et al., "Advanced Organic Chemistry", 3rd Ed. Part A: Structure and Mechanisms, Plenum Press, New York (1993).

H.F. Chambers et al., "Chapter 43 Antimicrobial Agents General Consideration", Goodman & Gilman's The Pharmacological Basis of Therapeutics, 10th ed. Hardman JG, Limbird LE and Gilman AG, Eds., McGraw-Hill, pp. 1143-1170 (2001).

H.F. Chambers et al., "Chapter 47 Antimicrobial Agents Protein Synthesis Inhibitors and Miscellaneous Antibacterial Agents", Goodman & Gilman's The Pharmacological Basis of Therapeutics, 10th ed. Hardman JG, Limbird LE and Gilman AG, Eds., McGraw-Hill, pp. 1239-1271(2001).

Selvakumar et al., "Influence of Ethylene-Oxy Spacer Group on the Activity of Linezolid: Synthesis of Potent Antibacterials Processing a Theiocarbonyl Group", Bioorganic & Medicinal Chemistry Letters, vol. 13, pp. 4169-4172 (2003).

Hcaplus 141:207195: Meha et al "A prepaaton of (oxazolidinylmehyl) acetamide derivatives, useful as antmicrobial agents", Aug. 19, 2004.

M.E. Wolff et al., "Burger's Medicinal Chemistry, 5th ed., Part 1", John Wiley & Sons, pp. 975-977 (1995).

G.S. Banker et al., "Modern Pharmaceuticals, 3rd ed.", Marcel Dekker, New York, pp. 451 and 596 (1996).

Hawley's Condensed Chemical Dictionary, pp. 594 (1993).

Concise Encyclopedia Chemistry, (1993), p. 490, the term "Heterocycles".

Dictionary of Chemistry, McGraw-Hill, 2nd Edition (2003), p. 178, the term "heterocyclic compound".

R.T. Morrison et al., Lehrbuch der Organischen Chemie, 3, Auflage, pp. 38-39 (1986).

USE OF OXAZOLIDINONE-QUINOLINE HYBRID ANTIBIOTICS FOR THE TREATMENT OF ANTHRAX AND OTHER INFECTIONS

This application is a continuation application of U.S. patent application Ser. No. 12/987,611, filed Jan. 10, 2011, which is a divisional application of U.S. patent application Ser. No. 10/554,732, filed Jan. 5, 2007, which is a U.S. National Stage application under 35 U.S.C. §371 of International Application No. PCT/EP2004/003650, filed Apr. 6, 2004, which claims the benefit of U.S. provisional application Ser. No. 60/466,945, filed Apr. 30, 2003 and U.S. provisional application Ser. No. 60/530,822, filed Dec. 18, 2003, the disclosures of each of which are expressly incorporated by reference in their entireties.

The present invention describes the use of compounds in which the pharmacophores of quinolone and oxazolidinone are chemically linked together through a linker that is stable under physiological conditions for the treatment of anthrax and other infections.

Anthrax is an acute infectious disease caused by the spore-forming bacterium *Bacillus anthracis*. Anthrax most commonly occurs in wild and domestic lower vertebrates (cattle, sheep, goats, camels, antelopes, and other herbivores), but it can also occur in humans when they are exposed to infected animals or tissue from infected animals. *Bacillus anthracis*, the etiologic agent of anthrax, is a large, gram-positive, non-motile, spore-forming bacterial rod. The three virulence factors of *B. anthracis* are edema toxin, lethal toxin and a capsular antigen. Human anthrax has three major clinical forms: cutaneous, inhalation, and gastrointestinal. If left untreated, anthrax in all forms can lead to septicemia and death. Recently, anthrax has become of considerable interest, because it is considered to be a potential agent for use in biological warfare.

The present invention provides the use of compounds of Formula (I) for the treatment of anthrax and other infections:

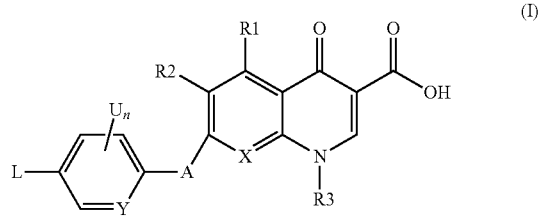

(I)

wherein

A is a direct bond, a NH, O, S, SO, $SO_2$, $SO_2NH$, $PO_4$, —NH—CO—NH—, —CO—NH—, —CO—, —CO—O—, —NH—CO—O—, —O—Z-hetero-cycloalkylen, an alkylen group, an alkenylen group, an alkinylen group, a heteroalkylen group, an arylen group, a heteroarylen group, a cycloalkylen group, a heterocycloalkylen group, an alkylarylen group or a heteroarylalkylen group or a combination of two or more of these atoms or groups;

L is selected from the following groups:

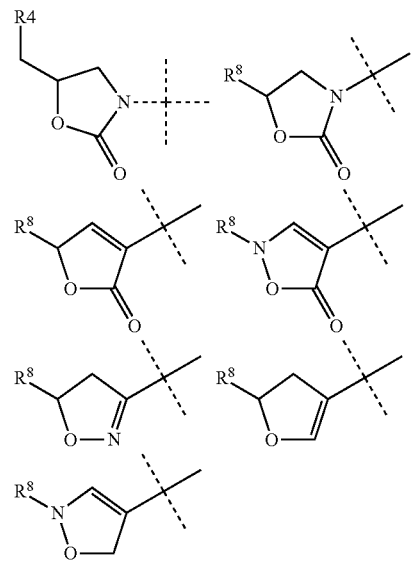

X is CR5 or N;
Y is CR6 or N;
U is F or Cl;
Z is a $C_{1-4}$ alkylene group, a $C_{2-4}$ alkenylene group, a $C_{2-4}$ alkynylene group or a $C_{1-4}$ heteroalkylene group, all of which may be substituted by one or more hydroxy or amino groups;
n is 0, 1, 2 or 3;
R1 is H, F, Cl, Br, I, OH, $NH_2$, an alkyl group or a heteroalkyl group;
R2 is H, F or Cl;
R3 is H, an alkyl group, an alkenyl group, an alkinyl group, a heteroalkyl group, a cycloalkyl group, a heterocycloalkyl group, an aryl group, a heteroaryl group, an alkylaryl group or a heteroarylalkyl group; all of which may be substituted with one, two or more halogen atoms like F or Cl;
R4 is a heteroalkyl group, a cycloalkyl group, a heterocycloalkyl group, an aryl group, a heteroaryl group, an alkylaryl group or a heteroarylalkyl group;
R5 is H, F, Cl, OH, $NH_2$, an alkyl group or a heteroalkyl group, or
R3 and R5 can be linked via an alkylen, an alkenylen or a heteroalkylen group or be a part of a cycloalkylen or heterocyclo-alkylen group; in case R3 is no H and R5 is no H, F, OH, $NH_2$ or Cl;
R6 is H, F, Cl or OMe;
R8 is a $C_{1-6}$ heteroalkyl or a heteroarylalkyl group;
or a pharmacologically acceptable salt, solvate, hydrate or formulation thereof.

It should be appreciated that certain compounds of Formula (I), or Formula (II) or (III) of the present application, may have tautomeric forms from which only one might be specifically mentioned or depicted in the following description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). Further, some compounds may display polymorphism. All these tautomeric forms, geometrical or optical isomers (as well as racemates and diastereomers) and polymorphous forms are included in the invention.

The term alkyl refers to a saturated or unsaturated (i.e. alkenyl and alkinyl) straight or branched chain alkyl group, containing from one to ten, preferably one to six carbon atoms for example methyl, ethyl, propyl, iso-propyl, butyl, iso-butyl, sec-butyl, tert-butyl, n-pentyl, iso-pentyl n-hexyl, 2,2-dimethylbutyl, n-octyl; ethenyl (vinyl), propenyl (allyl), iso-propenyl, n-pentyl, butenyl, isoprenyl or hexa-2-enyl; ethinyl, propinyl or butinyl groups. Any alkyl group as defined herein may be substituted with one, two or more substituents, for example F, Cl, Br, I, $NH_2$, OH, SH or $NO_2$.

The terms alkenyl and alkinyl refer to an unsaturated straight or branched chain alkyl group (having one, two or more double and/or triple bonds, an alkenyl preferably having one or two double bonds and an alkinyl preferably having one or two triple bonds), containing from two to ten, preferably two to six carbon atoms for example: ethenyl (vinyl), propenyl (allyl), iso-propenyl, n-pentenyl, butenyl, isoprenyl or hexa-2-enyl; ethinyl, propinyl or butinyl groups. Any alkenyl or alkinyl group as defined herein may be substituted with one, two or more substituents, for example F, Cl, Br, I, $NH_2$, OH, SH or $NO_2$.

The term heteroalkyl refers to an alkyl group as defined herein where one or more carbon atoms are replaced by an oxygen, nitrogen, phosphorous or sulphur atom for example an alkoxy group such as methoxy, ethoxy, propoxy, iso-propoxy, butoxy or tert.-butoxy, an alkoxyalkyl group such as methoxymethyl, ethoxymethyl, 1-methoxyethyl, 1-ethoxyethyl, 2-methoxyethyl or 2-ethoxyethyl, an alkylamino group such as methylamino, ethylamino, propylamino, isopropylamino, dimethylamino or diethylamino, an alkylthio group such as methylthio, ethylthio or isopropylthio or a cyano group. It may also refer to one of the above groups containing a keto group. The term heteroalkyl furthermore refers to a group derived from a carboxylic acid or carboxylic acid amide such as acetyl, propionyl, acetyloxy, propionyloxy, acetylamino or propionylamino, a carboxyalkyl group such as carboxymethyl, carboxyethyl or carboxypropyl, a carboxyalkyl ester, an alkylthiocarboxyamino group, an alkoxyimino group, an alkylaminothiocarboxyamino group or an alkoxycarbonylamino group. Any heteroalkyl group as defined herein may be substituted with one, two or more substituents, for example F, Cl, Br, I, $NH_2$, OH, SH or $NO_2$.

The term cycloalkyl refers to a saturated or partially unsaturated (having one, two or more double and/or triple bonds), cyclic group with one, two or more rings, having three to 14 carbon ring-atoms, preferably from five or six to ten carbon ring-atoms, for example cyclopropyl, cyclobutyl, cyclopentyl, cyclohexyl, tetralin, cyclopentenyl or cyclohex-2-enyl groups. Any cycloalkyl group as defined herein may be substituted with one, two or more substituents, for example F, Cl, Br, I, OH, $NH_2$, SH, $N_3$, $NO_2$, alkyl groups such as methyl or ethyl, heteroalkyl groups such as methoxy, methylamino, dimethylamino, cyanide, or a group of the formula —OR7, wherein R7 is hydrogen, a group of formula $PO_3R^9_2$ or $SO_3R^{10}$ or a heteroalkyl group carrying at least one OH, $NH_2$, $SO_3R^{10}$, $PO_3R^9_2$ or COOH group, wherein $R^9$ is H, alkyl, cycloalkyl, aryl, aralkyl, and wherein $R^{10}$ is H, alkyl, cycloalkyl, aryl, aralkyl.

The term heterocycloalkyl refers to a cycloalkyl group as defined herein where one, two or more carbon ring-atoms are replaced by one, two or more oxygen, nitrogen, phosphorous or sulphur atoms or $S(O)_{1-2}$ groups for example piperidino, morpholino or piperazino groups, preferably such groups contain 1 or 2 nitrogen atoms.

The term aryl refers to an aromatic cyclic group with one, two or more rings, having five to 14 carbon ring-atoms preferably from five or six to ten carbon ring-atoms, for example phenyl or naphthyl groups. Any aryl group as defined herein may be substituted with one, two or more substituents, for example F, Cl, Br, I, OH, $NH_2$, SH, $N_3$, $NO_2$, alkyl groups such as methyl or ethyl, heteroalkyl groups such as methoxy, methylamino, dimethylamino or cyanide.

The term heteroaryl refers to an aryl group as defined herein where one, two or more ring-carbon atoms are replaced by an oxygen, nitrogen, boron, phosphorous or sulphur atom, for example pyridyl, imidazolyl, pyrazolyl, quinolinyl, isoquinolinyl, pyrrolyl, oxazolyl, isoxazolyl, thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl and pyridazinyl groups.

The terms arylalkyl, alkylaryl and heteroarylalkyl, heteroalkylaryl refer to groups that comprise both aryl or, respectively, heteroaryl as well as alkyl and/or heteroalkyl and/or cycloalkyl and/or heterocycloalkyl groups.

Preferred embodiments of the present invention are compounds of Formula (I), wherein A is a bond, a NH, O, S, SO, $SO_2$, $SO_2NH$, $PO_4$, —NH—CO—NH—, —CO—NH—, —CO—, —CO—O—, —NH—CO—O—, an alkylen group, an alkenylen group, an alkinylen group, a heteroalkylen group, an arylen group, a heteroarylen group, a cycloalkylen group, a heterocycloalkylen group, an alkylarylen group or a heteroarylalkylen group or a combination of two or more of these atoms or groups;

L is

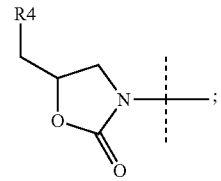

X is CR5 or N;
Y is CR6 or N;
U is F or Cl;
n is 0, 1, 2 or 3;
R1 is H, F, Cl, Br, I, OH, $NH_2$, an alkyl group or a heteroalkyl group;
R2 is H, F or Cl;
R3 is H, an alkyl group, an alkenyl group, an alkinyl group, a heteroalkyl group, a cycloalkyl group, a heterocycloalkyl group, an aryl group, a heteroaryl group, an alkylaryl group or a heteroarylalkyl group;
R4 is a heteroalkyl group, a cycloalkyl group, a heterocycloalkyl group, an aryl group, a heteroaryl group, an alkylaryl group or a heteroarylalkyl group;
R5 is H, F, Cl, OH, $NH_2$, an alkyl group or a heteroalkyl group, or
R3 and R5 can be linked via an alkylen, an alkenylen or a heteroalkylen group or be a part of a cycloalkylen or heterocyclo-alkylen group; in case R3 is no H and R5 is no H, F, OH, $NH_2$ or Cl;
R6 is H, F, Cl or OMe;
or a pharmacologically acceptable salt, solvate, hydrate or formulation thereof for the treatment of anthrax.

Preferred and/or advantageous embodiments of the invention are subject-matter of the subclaims.

Preferred are compounds of Formula (I), wherein R1 is H or NH$_2$ (especially H).

Further preferred are compounds of Formula (I), wherein R2 is H or F (especially F).

Moreover preferred are compounds of Formula (I), wherein R3 is an ethyl, a 2-propyl, a C3-C6 cycloalkyl, a phenyl or a pyridyl group. All these groups may be substituted by one, two or more fluorine atoms or amino groups.

Moreover preferred are compounds of Formula (I), wherein R3 is a cyclopropyl group.

Further preferred are compounds of Formula (I), wherein R3 and R5 together form a bridge of the formula —O—CH$_2$—N(Me)- or —O—CH$_2$—CH(Me)-. Herein, the preferred stereochemistry at the chiral center is the one giving the (S) configuration in the final compound.

Further preferred are compounds of Formula (I), wherein R4 is a group of the formula —NHCOCH=CHAryl, —OHeteroaryl (especially -oxa-3-oxazol), —NHSO$_2$Me, —NHCOOMe, NHCS$_2$Me, NHCSNH$_2$, —NHCSOMe or —NHCOMe.

Especially preferred are compounds of Formula (I), wherein R4 is an acetylamino group.

Further preferred are compounds of Formula (I), wherein the absolute configuration at C-5 of the oxazolidinone ring is (S) according to the Cahn-Ingold-Prelog nomenclature system.

Moreover preferred are compounds of Formula (I), wherein R5 is H, F, Cl or a methoxy group which may be substituted by one, two or three fluorine atoms or a CF$_3$ group.

Further preferred are compounds of Formula (I), wherein X is N or CH.

Further preferred are compounds of Formula (I), wherein Y is N or CF (especially CF).

Further preferred are compounds of Formula (I), wherein n is 0.

Further preferred are compounds of Formula (I), wherein A is a bond.

Further preferred are compounds of Formular (I), wherein A is a group of the formula

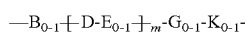

wherein the group B is NH, O, S, SO, SO$_2$, SO$_2$NH, an alkylene, which may be substituted by one, two or more fluorine atoms or a heteroalkylen group, which may be substituted by one, two or more fluorine atoms and/or at the optionally present nitrogen atoms by an alkyl or an acyl group;

the groups D independently of each other are optionally anellated heterocycloalkylen groups with 1, 2, 3 or 4 nitrogen atoms, which heterocycloalkylen groups may each be substituted by one, two or more fluorine atoms and/or which each may be substituted at one, two, three or four nitrogen atoms by an alkyl or an acyl group;

the groups E independently of each other are NH, O, S, SO, SO$_2$, SO$_2$NH, an alkylene, which may be substituted by one, two or more fluorine atoms or a heteroalkylen group, which may be substituted by one, two or more fluorine atoms and/or at the optionally present nitrogen atoms by an alkyl or an acyl group;

the groups G independently of each other are optionally anellated heterocycloalkylen groups with 1, 2, 3 or 4 nitrogen atoms, which heterocycloalkylen groups may each be substituted by one, two or more fluorine atoms and/or which each may be substituted at one, two, three or four nitrogen atoms by an alkyl or an acyl group;

the group K is NH, O, S, SO, SO$_2$, SO$_2$NH, an alkylene, which may be substituted by one, two or more fluorine atoms or a heteroalkylen group, which may be substituted by one, two or more fluorine atoms and/or at the optionally present nitrogen atoms by an alkyl or an acyl group; and m=1, 2, 3 or 4.

Moreover preferred are compounds of Formula (I), wherein A is a cycloalkylen or a alkylcycloalkylen group that contains 2, 3 or 4 heteroatoms (preferred O, N and S) and may be substituted by one, two or more fluorine atoms and the nitrogen atoms may be substituted by an alkyl or an acyl group.

Further preferred are compounds of Formula (I), wherein A is selected from the following groups which may be further substituted by one, two or more fluorine atoms or by an alkyl group which may be substituted by one, two or more fluorine atoms, and wherein the amino groups may be substituted by an alkyl or an acyl group:

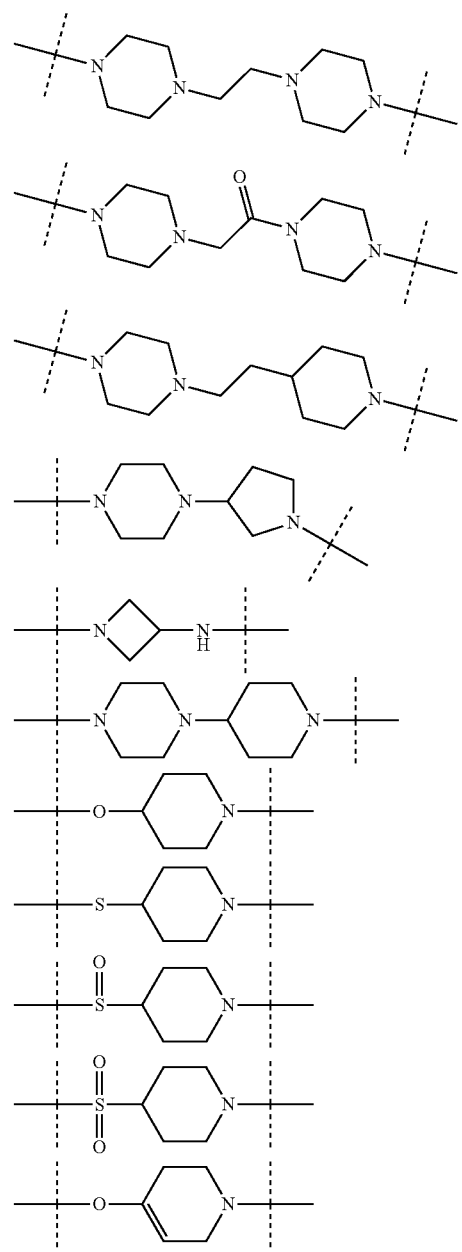

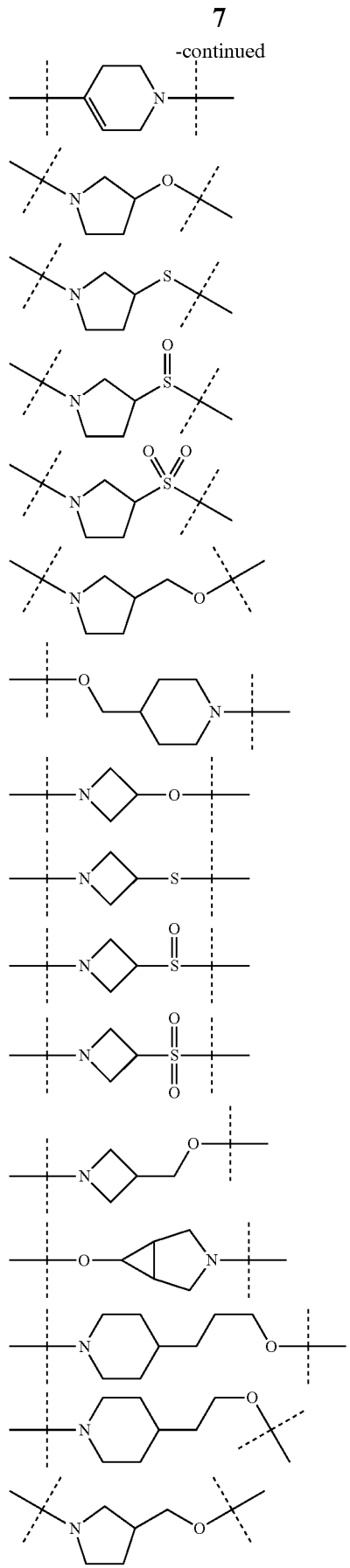

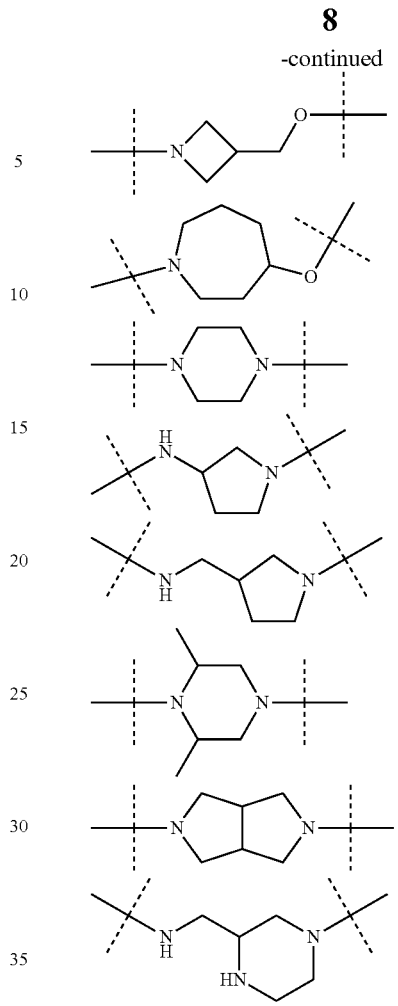

Moreover preferred are compounds of Formula (I), wherein A is a group of the formula —V—W—, wherein V is a direct bond or a group of the formula NH, O, S, SO, SO$_2$, SO$_2$NH, PO$_4$, —NH—CO—NH—, —CO—NH—, —CO—, —CH$_2$—, —CO—O—, —(CH$_2$)$_{1-3}$—O—, —CH=CH—C(O)—, or —NH—CO—O— and W is a heterocycloalkyl group with 4 to 7 ring atoms or a alkylheterocycloalkyl group with 4 to 7 ring atoms and 1 to 4 carbon atoms in the alkyl chain; all these groups may be substituted by 1, 2, 3 or 4 fluorine atoms, methyl or methoxy groups.

Further preferred are compounds of Formula (I), wherein A is a group of the formula

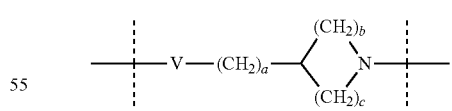

wherein V is a group of the formula NH, O, S, SO, SO$_2$, SO$_2$NH, PO$_4$, —NH—CO—NH—, —CO—NH—, —CO—, —CH$_2$—, —CO—O—, —(CH$_2$)$_{1-3}$—O—, —CH=CH—C(O)—, or —NH—CO—O—; a is 0, 1, 2, 3 or 4; b is 0, 1, 2, 3 or 4; c is 0, 1, 2, 3 or 4 and 1, 2, 3 or 4 hydrogen atoms may be substituted by F, a methyl- or a methoxy group.

Moreover preferred are compounds as described here, wherein V is NH, O, S, SO or SO$_2$.

Especially preferred are compounds as described here, wherein V is O or NH; a is 0 or 1; b is 1 or 2 and c is 1 or 2.

Moreover preferred are compounds as described here, wherein A is a group of the formula OCH₂Het, wherein Het is an optionally substituted heterocycloalkylen group with 4, 5, 6 or 7 ring atoms.

Another preferred embodiment of the present invention are compounds of Formula (II):

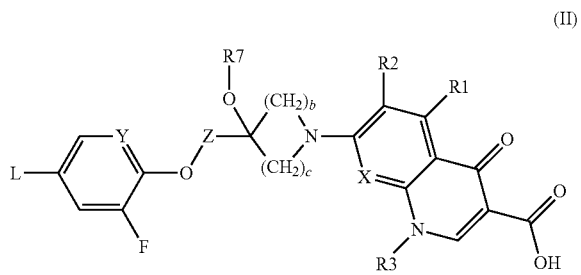

wherein
L is selected from following groups:

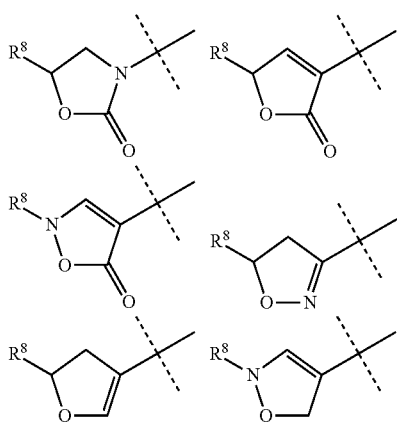

X is CR5 or N;
Y is CR6 or N;
Z is a $C_{1-4}$ alkylene group, a $C_{2-4}$ alkenylene group, a $C_{2-4}$ alkynylene group or a $C_{1-4}$ heteroalkylene group, all of which may be substituted by one or more hydroxy or amino groups;
b is 1, 2 or 3;
c is 1, 2 or 3;
R1 is H, F, Cl, Br, I, OH, NH₂, an alkyl group or a heteroalkyl group;
R2 is H, F or Cl;
R3 is H, an alkyl group, an alkenyl group, an alkinyl group, a heteroalkyl group, a cycloalkyl group, a heterocycloalkyl group, an aryl group, a heteroaryl group, an alkylaryl group or a heteroarylalkyl group; all of which may be substituted with one, two or more halogen atoms like F or Cl.
R5 is H, F, Cl, OH, NH₂, an alkyl group or a heteroalkyl group, or
R3 and R5 can be linked via an alkylen, an alkenylen or a heteroalkylen group or be a part of a cycloalkylen or heterocyclo-alkylen group; in case R³ is no H and R⁵ is no H, F, OH, NH₂ or Cl;
R6 is H, F, Cl or OMe;
R7 is hydrogen, a group of formula $PO_3R^9_2$ or $SO_3R^{10}$ or a heteroalkyl group carrying at least one OH, NH₂, $SO_3R^{10}$, $PO_3R^9_2$ or COOH group, wherein $R^9$ is H, alkyl, cycloalkyl, aryl, aralkyl, and wherein $R^{10}$ is H, alkyl, cycloalkyl, aryl, aralkyl,
R8 is a $C_{1-6}$ heteroalkyl or a heteroarylalkyl group;
or a pharmacologically acceptable salt, solvate, hydrate or formulation thereof.

Further preferred are compounds of Formula (II), wherein R1 is H.

Further preferred are compounds of Formula (II), wherein R2 is F or H.

Moreover preferred are compounds of Formula (II), wherein R3 is an ethyl, a 2-propyl, a C3-C6 cycloalkyl, a phenyl or a pyridyl group. All these groups may be substituted by one, two or more fluorine atoms or amino groups.

Moreover preferred are compounds of Formula (II), wherein R3 is a cyclopropyl group.

Further preferred are compounds of Formula (II), wherein R3 and R5 together form a bridge of the formula —O—CH₂—N(Me)- or —O—CH₂—CH(Me)-. Herein, the preferred stereochemistry at the chiral center is the one giving the S configuration in the final compound.

Moreover preferred are compounds of Formula (II), wherein R7 is hydrogen or a group of formula $PO_3H_2$, $SO_3R^{10}$, $PO_3R^9_2$, $CH_2OPO_3H_2$ or $COCH_2CH_2COOH$, wherein $R^9$ is H, alkyl, cycloalkyl, aryl, aralkyl, and wherein $R^{10}$ is H, alkyl, cycloalkyl, aryl, aralkyl or together with the oxygen to which it is bound forms an ester of a naturally occurring amino acid or a derivative thereof (e.g. dimethyl aminoglycine).

Further preferred are compounds of Formula (II), wherein $R^8$ is a group of the formula —CH₂NHCOCH=CHAryl, —CH₂OHeteroaryl (especially -oxa-3-oxazol), —CH₂NHSO₂Me, —CH₂NHCOOMe, —CH₂NHCS₂Me, —CH₂NHCSNH₂, —CH₂NHCSOMe or —CH₂NHCOMe.

Especially preferred are compounds of Formula (II), wherein L has the following structure:

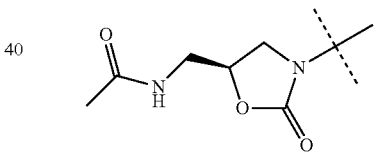

Moreover preferred are compounds of Formula (II), wherein R5 is H, F, Cl or a methoxy group which may be substituted by one, two or three fluorine atoms.

Further preferred are compounds of Formula (II), wherein X is N or CH.

Moreover preferred are compounds of Formula (II), wherein Y is CH.

Further preferred are compounds of Formula (II), wherein Z is CH₂ or CH₂CH₂.

Especially preferred are compounds of Formula (III)

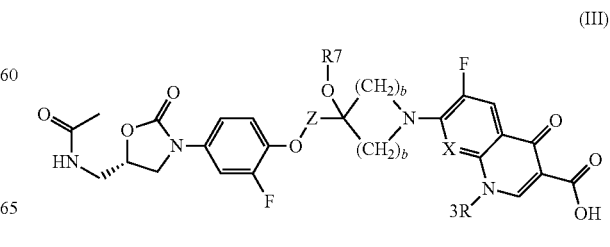

wherein Z is $CH_2$ or $CH_2CH_2$; X is CH, N or C—OMe and R3 is cyclopropyl or X is CR5 and R5 and R3 together form a bridge of the formula —O—$CH_2$—CH(Me)-, wherein, the preferred stereochemistry at the chiral center is the one giving the S configuration in the final compound and b, c and R7 are the same as defined above.

The present invention also relates to pharmacologically acceptable salts, or solvates and hydrates, respectively, and to compositions and formulations of compounds of Formula (I), (II), or (III). The present invention describes procedures to produce pharmaceutically useful agents, which contain these compounds, as well as the use of these compounds for the production of pharmaceutically useful agents.

The pharmaceutical compositions according to the present invention contain at least one compound of Formula (I), (II) or (III) as the active agent and optionally carriers and/or diluents and/or adjuvants. Optionally the pharmaceutical compositions according to the present invention may also contain additional known antibiotics.

Examples of pharmacologically acceptable salts of sufficiently basic compounds of Formula (I) and of compounds of Formula (II) or (III) are salts of physiologically acceptable mineral acids like hydrochloric, hydrobromic, sulfuric and phosphoric acid; or salts of organic acids like methanesulfonic, p-toluenesulfonic, lactic, acetic, trifluoro-acetic, citric, succinic, fumaric, maleic and salicylic acid. Further, a sufficiently acidic compound of Formula (I) may form alkali or earth alkaline metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of Formula (II) or (III). Compounds of Formula (I), (II) or (III) may be solvated, especially hydrated. The hydratisation can occur during the process of production or as a consequence of the hygroscopic nature of the initially water free compounds of Formula (I), (II) or (III). The compounds of Formula (I), (II) or (III) contain asymmetric C-atoms and may be present either as achiral compounds, mixtures of diastereomers, mixtures of enantiomers or as optically pure compounds.

The present invention also relates to pro-drugs which are composed of a compound of Formula (I), (II) or (III) and at least one pharmacologically acceptable protective group which will be cleaved off under physiological conditions, such as an alkoxy-, aralkyloxy-, acyl-, acyloxymethyl group (e.g. pivaloyloxymethyl), an 2-alkyl-, 2-aryl- or 2-aralkyl-oxycarbonyl-2-alkylidene ethyl group or an acyloxy group as defined herein, e.g. ethoxy, benzyloxy, acetyl or acetyloxy or, especially for a compound of Formula (I), for hydroxy group (ROH), a sulfate, a phosphate ($ROPO_3$ or $ROCH_2OPO_3$) or an ester of an amino acid. Especially preferred are pro-drugs of the hydroxy group of a compound of Formula (II) or (III) wherein R7 is H.

As mentioned above, therapeutically useful agents that contain compounds of Formula (I), (II) or (III), their solvates, salts or formulations are also comprised in the scope of the present invention. In general, compounds of Formula (I), (II) or (III) will be administered by using the known and acceptable modes known in the art, either alone or in combination with any other therapeutic agent. Such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), trans-dermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatin, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilisation, e.g. UV stabilizers, emulsifiers, sweetener, aromatisers, salts to change the osmotic pressure, buffers, coating additives and antioxidants.

A daily dosage per patient of about 1 mg to about 4000 mg especially about 50 mg to 3 g is usual with those of ordinary skill in the art appreciating that the dosage will depend also upon the age, conditions of the mammals, and the kind of diseases being treated or prevented. The daily dosage can be administrated in a single dose or can be divided over several doses. An average single dose of about 50 mg, 100 mg, 250 mg, 500 mg, 1000 mg and 2000 mg can be contemplated.

The invention also relates to a method of treating a disorder selected from a bacterial infection, a protozoal infection, and disorders related to bacterial infections or protozoal infections, in a mammal, fish, or bird which comprises administering to the mammal, fish or bird a combination comprising a compound of Formula (I), (II) or (III) and another antibiotic, wherein the amounts of the compound and of the other antibiotic are together therapeutically effective in treating the disorder. In further embodiments, the compound of the invention may administered prior to, with or after the other antibiotic. Examples of suitable other antibiotics include, but are not limited to, beta-lactams, vancomycin, aminoglycosides, quinolones, chloramphenicol, tetracyclines and macrolides.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "infection(s)", "bacterial infection(s)", "protozoal infection(s)", and "disorders related to bacterial infections or protozoal infections" include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casselflavus, S. epidermidis, S. haemolyticus,* or *Peptosfreptococcus* spp.;

pharyngitis, rheumatic fever, and glomerulonephritis related to infection by *Streptococcus pyogenes*, Groups C and G streptococci, *Corynebacferium diphtheriae*, or *Acfinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyficus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. hemolyticus*, etc.), *Streptococcus pyogenes, Streptococcus agalactiae*, Streptococcal groups C-F (minute colony streptococci), viridans streptococci, *Corynebacterium minutissimum, Closfridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidurn, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Closfridium perfringens* or *Bacteroides* spp.; and atherosclerosis or cardiovascular disease related to infection by *Helicobacter pylori* or *Chlamydia pneumoniae*.

Preferred is the use of a compound according to Formula (I), (II) or (III) for the treatment of infections that are mediated by Gram-negative bacteria such as *E. coli, Klebsiella pneumoniae* and other enterobacteriaceae, *Haemophilus influenzae, Moraxella catarrhalis, Acinetobacter* spp., *Stenothrophomonas maltophilia, Neisseria gonorrhoeae, Neisseria menigitidis, Helicobacter pylori, Campylobacter* spp., *Mycoplasma* spp. and *Legionella pneumophilia* or Gram-positives such as *Bacillus cereus, Bacillus anthracis, Strep. pneumoniae, Corynebacterium* spp., *Propionibacterium acnes* and *Listeria monocytogenes*.

In the following the invention is described in more detail with reference to examples. These examples are intended for illustration only and are not to be construed as any limitation. The Examples were synthesized according to the procedures described in WO03032962, WO03031443, U.S. 60/530,822 and C. Hubschwerlen et al. Bioorg. Med. Chem. 2003, 11, 2313-2319.

The compounds of Formula (II) and (III) can be synthesized according to the following reaction scheme:

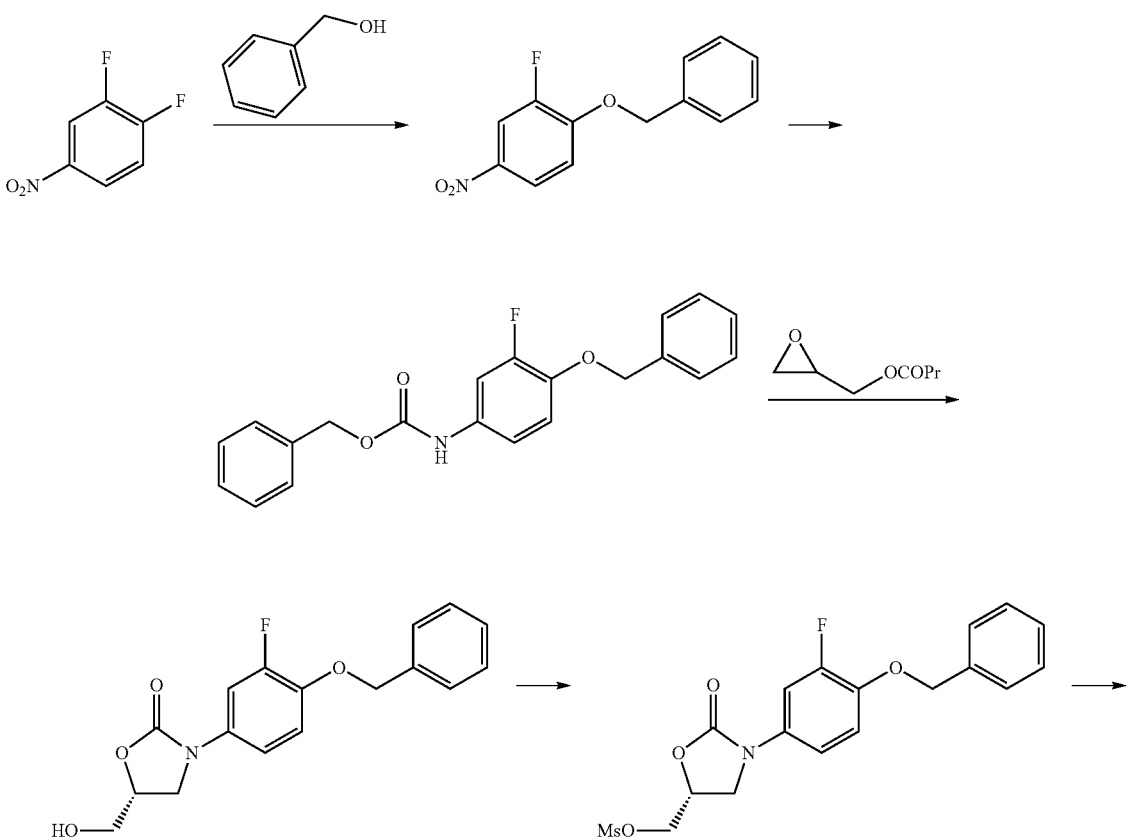

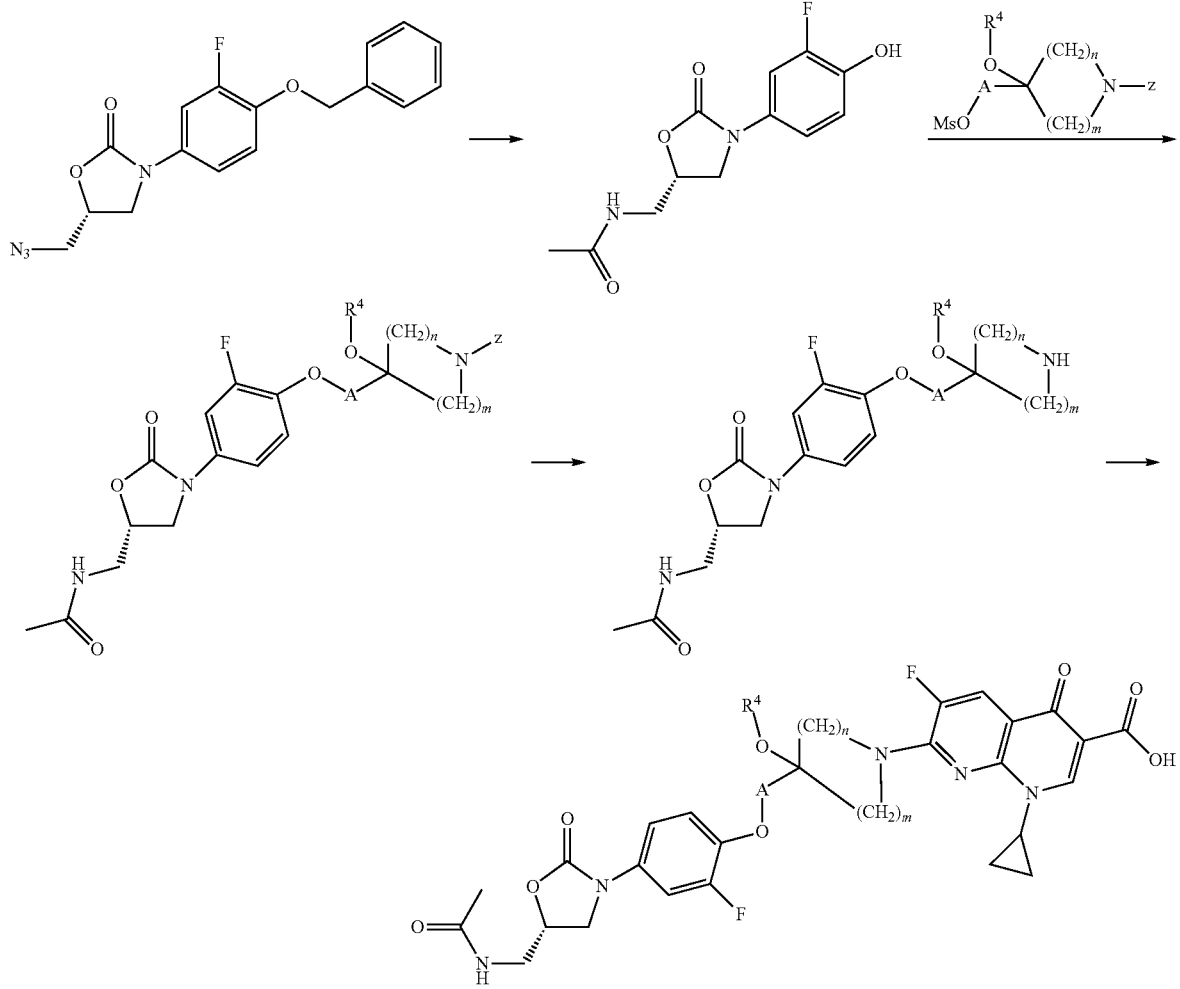

Reaction Conditions:

Step 1: CH$_2$Cl$_2$, KOH (50%), 3 h, rt; 97%. step 2: H$_2$, Pt/C, 20 h, rt; followed by Z—Cl, acetone/water, NaHCO$_3$, 12 h, rt, 98%. step 3: n-BuLi, −60° C., 24 h, 80%. step 4: MsCl, triethylamine, CH$_2$Cl$_2$; 100%. step 5: NaN$_3$ in DMF, 90° C., cat. Bu$_4$NI, 5 h, 90%. step 6: H$_2$, Pd(OH)$_2$, THF, MeOH, 24 h, followed by AcOH, Ac$_2$O, rt, 2 h, 70%. step 7: DMF, NaH, 70° C., 12 h, 75%. step 8: H$_2$, Pd(OH)$_2$, MeOH, THF, 24 h, RT, 100%. step 9: N-Methylpyrrolidinone, 1-Cyclopropyl-7-chloro-6-fluoro-1,4-dihydro-4-oxo-1,8-naphthydrin-3-carboxylic acid (commercially available), TMS-Cl, Hünig Base or K$_2$CO$_3$, 80° C., 5 h, 80%.

EXAMPLES

Example 1

7-(4-{4-[5-(acetylamino-methyl)-2-oxo-oxazolidin-3-yl]-2-fluoro-phenyl}-piperazin-1-yl)-1-cyclopropyl-6-fluoro-4-oxo-1,4-dihydro-quinoline-3-carboxylic acid

Example 2

9-(4-{4-[5-(acetylamino-methyl)-2-oxo-oxazolidin-3-yl]-2-fluoro-phenyl}-piperazin-1-yl)-8-fluoro-3-methyl-6-oxo-2,3-dihydro-6H-1-oxa-3a-aza-phenalene-5-carboxylic acid

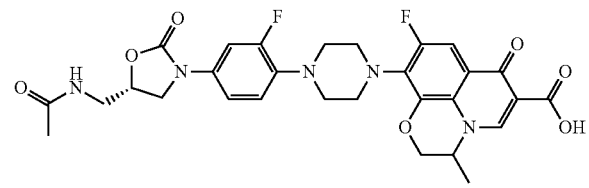 [SMILES: CC(=O)NC[C@H]1CN(c2ccc(N3CCN(c4c(F)cc5c(=O)c(C(=O)O)cn6c5c4OCC6C)CC3)c(F)c2)C(=O)O1]

Example 3

7-((3R,S)-3-{4-[(5S)-5-(acetylamino-methyl)-2-oxo-oxazolidin-3-yl]-2-fluoro-phenylcarbamoyl}-piperazin-1-yl)-1-cyclopropyl-6-fluoro-4-oxo-1,4-dihydro-quinoline-3-carboxylic acid

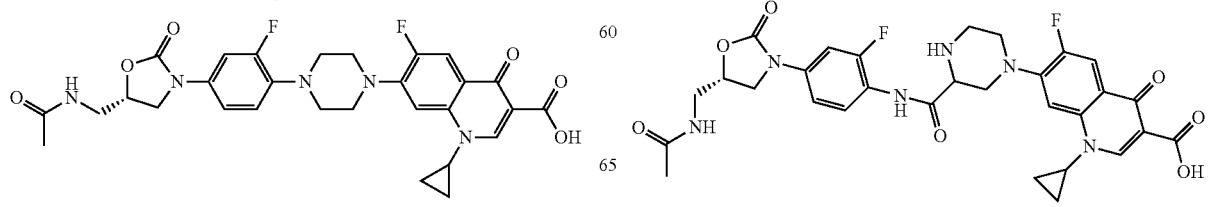

Example 4

7-[(3R)-3-{4-[(5S)-5-(Acetylamino-methyl)-2-oxo-oxazolidin-3-yl]-2-fluoro-phenylamino}-pyrrolidin-1-yl]-1cyclopropyl-6-fluoro-4-oxo-1,4-dihydro-quinoline-1-carboxylic acid

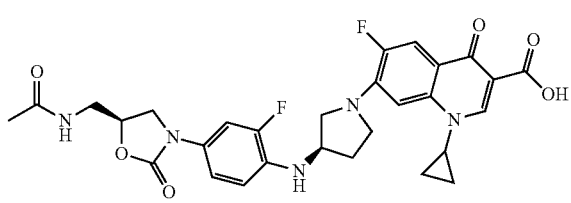 [SMILES: CC(=O)NC[C@H]1CN(c2ccc(N[C@@H]3CCN(c4cc5c(cc4F)c(=O)c(C(=O)O)cn5C4CC4)C3)c(F)c2)C(=O)O1]

Example 5

7-(4-{4-[(5S)-5-(Acetylamino-methyl)-2-oxo-oxazolidin-3-yl]-2-fluoro-phenyl}-piperazin-1-yl)-6-fluoro-1-(5-fluoro-pyridin-2-yl)-4-oxo-1,4-dihydro-quinoline-3-carboxylic acid

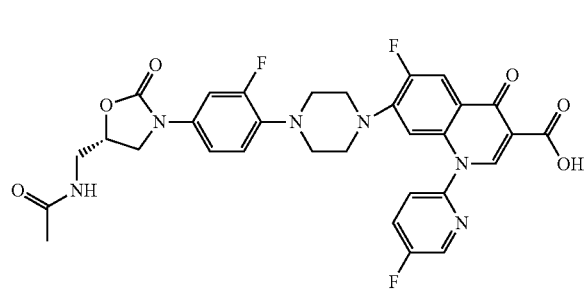 [SMILES: CC(=O)NC[C@H]1CN(c2ccc(N3CCN(c4cc5c(cc4F)c(=O)c(C(=O)O)cn5-c4ccc(F)cn4)CC3)c(F)c2)C(=O)O1]

Example 6

7-(4-{(5S)-5-(Acetylamino-methyl)-2-oxo-oxazolidin-3-yl]-2-fluoro-phenyl}-piperazin-1-yl)-1-(2,4-difluoro-phenyl)-6-fluoro-4-oxo-1,4-dihydro-quinoline-3-carboxylic acid

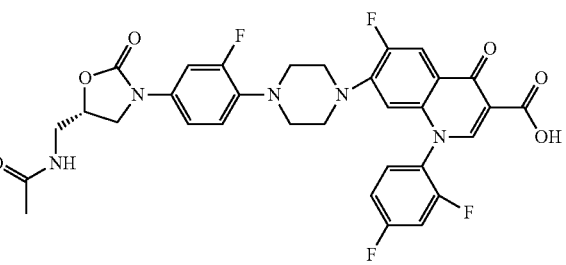

Example 7

7-(4-{4-[(5S)-5-(Acetylamino-methyl)-2-oxo-oxazolidin-3-yl]-2-fluoro-phenyl}-piperazin-1-yl)-1-cyclopropyl-8-methoxy-4-oxo-1,4-dihydro-quinoline-3-carboxylic acid

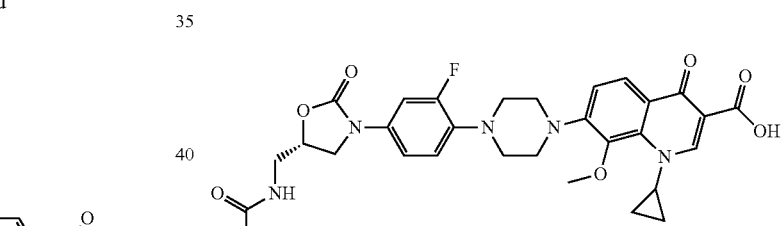

Example 8

9-(4-{4-[(5S)-5-(Acetylamino-methyl)-2-oxo-oxazolidin-3-yl]-2-fluoro-phenyl}-piperazin-1-yl)-8-fluoro-3-methyl-6-oxo-2,3-dihydro-6H-1-oxa-3,3a-diaza-phenalene-5-carboxylic acid

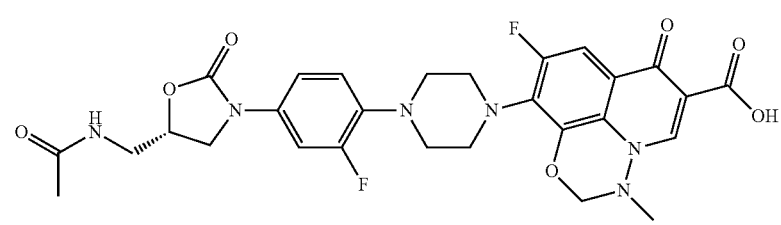 [SMILES: CC(=O)NC[C@H]1CN(c2ccc(N3CCN(c4c(F)cc5c(=O)c(C(=O)O)cn6c5c4OCN6C)CC3)c(F)c2)C(=O)O1]

19

Example 9

7-{(3RS)-3-[({4-[(5S)-5-(Acetylamino-methyl)-2-oxo-oxazolidin-3-yl]-2-fluoro-phenyl}-ethyl-amino)methyl]-piperazin-1-yl}-1-cyclopropyl-6-fluoro-4-oxo-1,4-dihydro-quinoline-3-carboxylic acid

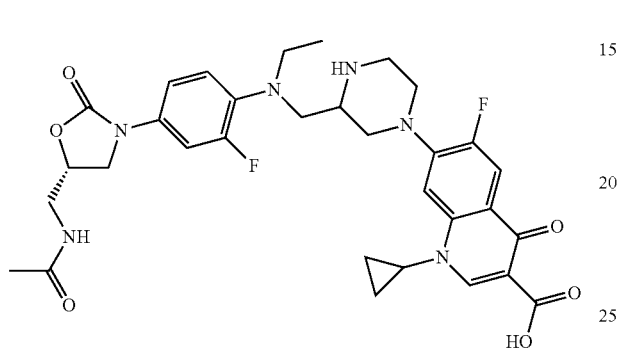

20

Example 10

7-(4-{[(5S)-5-(Acetylamino-methyl)-2-oxo-oxazolidin-3-yl]-2-fluoro-phenyl}-piperazin-1-yl)-1-cyclopropyl-6-fluoro-4-oxo-1,4-dihydro-[1,8]naphthyridine-3-carboxylic acid

Example 11

7-(4-[2-(4-{4-[5-(Acetylamino-methyl)-2-oxo-oxazolidin-3-yl]-2-fluoro-phenyl}-piperazin-1-yl)-ethyl]-piperazin-1-yl)-1-cyclopropyl-6-fluoro-4-oxo-1,4-dihydro-quinoline-3-carboxylic acid

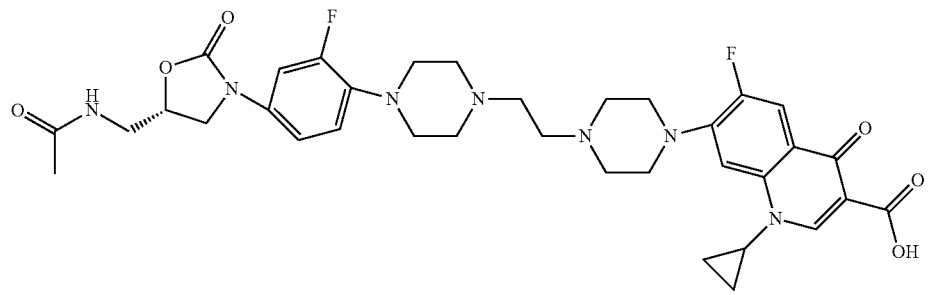 [SMILES: CC(=O)NC[C@H]1CN(c2ccc(N3CCN(CCN4CCN(c5cc6c(cc5F)c(=O)c(C(=O)O)cn6C5CC5)CC4)CC3)c(F)c2)C(=O)O1]

Example 12

7-[4-(4-{4-[(5S)-5-(Acetylamino-methyl)-2-oxo-oxazolidin-3-yl]-2-fluoro-phenyl}-piperazin-1-yl)-piperidin-1-yl]-1-cyclopropyl-6-fluoro-4-oxo-1,4-dihydro-quinoline-3-carboxylic acid

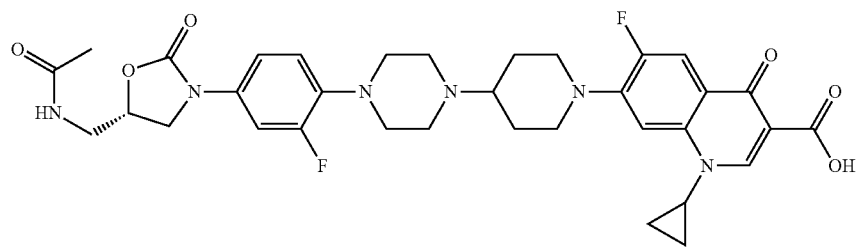 [SMILES: CC(=O)NC[C@H]1CN(c2ccc(N3CCN(C4CCN(c5cc6c(cc5F)c(=O)c(C(=O)O)cn6C5CC5)CC4)CC3)c(F)c2)C(=O)O1]

Example 13

7-[(3R,4R) and (3S,4S)-3-{4-[(5S)-5-(Acetylamino-methyl)-2-oxo-oxazolidin-3-yl]-2-fluoro-phenyl}-4-aminomethyl-pyrrolidin-1-yl]-1-cyclopropyl-6-fluoro-4-oxo-1,4-dihydro-quinolin-3-carboxylic acid

Example 15

7-(3-{4-[5(S)-5-(Acetylamino-methyl)-2-oxo-oxazolidin-3-yl]-2-fluoro-phenylamino}-azetidin-1-yl)-1-cyclopropyl-6-fluoro-4-oxo-1,4-dihydro-[1,8]naphthyridine-3-carboxylic acid

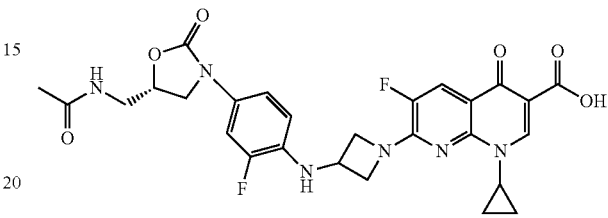

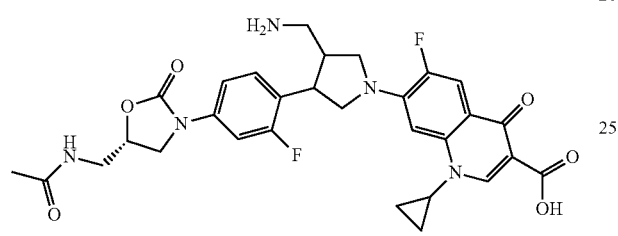

Example 16

7-[(3R)-3-{4-[(5S)-5-(Acetylamino-methyl)-2-oxo-oxazolidin-3-yl]-2-fluoro-phenylamino]-pyrrolidin-1-yl}-1-cyclopropyl-6-fluoro-4-oxo-1,4-dihydro-[1,8]-naphthyridine-3-carboxylic acid

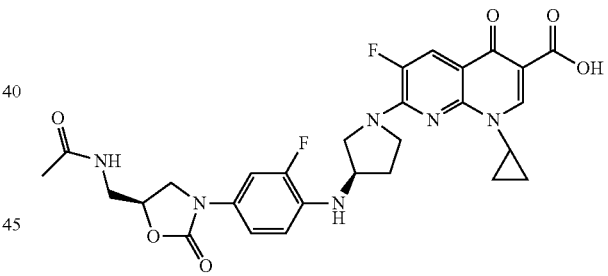

Example 14

7-{4-[2-(4-{4-[(5S)-5-(Acetylamino-methyl)-2-oxo-oxazolidin-3-yl]-2-fluoro-phenyl}-piperazin-1-yl)-2-oxo-ethyl]-piperazin-1-yl}-1-cyclopropyl-6-fluoro-4-oxo-1,4-dihydro-quinolone-3-carboxylic acid

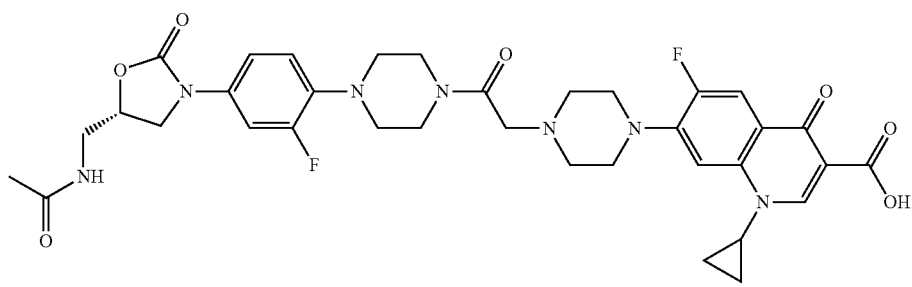 [SMILES: CC(=O)NC[C@H]1CN(c2ccc(N3CCN(C(=O)CN4CCN(c5cc6c(cc5F)c(=O)c(C(=O)O)cn6C5CC5)CC4)CC3)c(F)c2)C(=O)O1]

Example 17

7-[(3R,4S) and (3S,4R)-3-(−4{4-[(5S)-5-(Acetylamino-methyl)-2-oxo-oxazolidin-3-yl]-2-fluorophenyl}piperazine-1-carbonyl)-4-aminomethyl-pyrrolidin-1-yl]-1-cyclopropyl-6-fluoro-4-oxo-1,4-dihydro-quinoline carboxylic acid

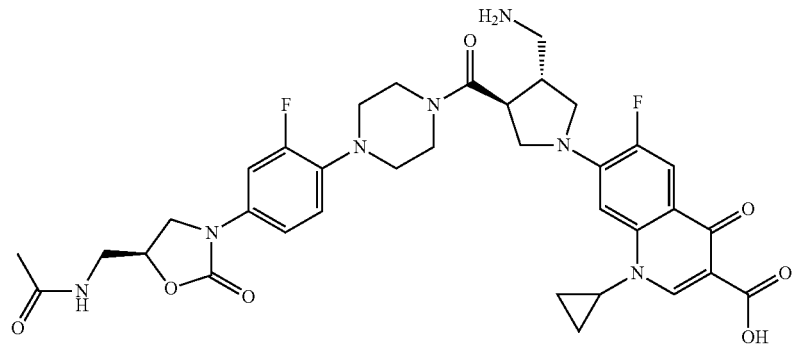 [SMILES: CC(=O)NC[C@H]1CN(c2ccc(N3CCN(C(=O)[C@@H]4CN(c5cc6c(cc5F)c(=O)c(C(=O)O)cn6C5CC5)C[C@H]4CN)CC3)c(F)c2)C(=O)O1]

Example 18

7-[(3R,4S) and (3S,4R)-3-(4-{4-[(5S)-5-(Acetylamino-methyl)-2-oxo-oxazolidin-3-yl]-2-fluorophenyl}-piperazine-1-carbonyl)-4-aminomethyl-pyrrolidin-1-yl)1-cyclopropyl-6-fluoro-4-oxo-1,4-dihydro-[1,8]naphthyridine-3-carboxylic acid

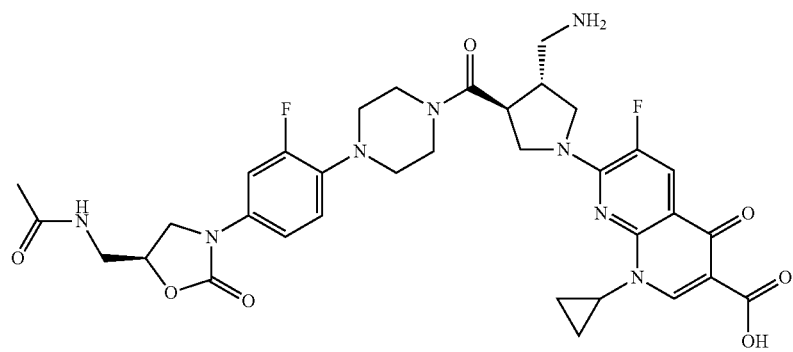 [SMILES: CC(=O)NC[C@H]1CN(c2ccc(N3CCN(C(=O)[C@@H]4CN(c5nc6c(cc5F)c(=O)c(C(=O)O)cn6C5CC5)C[C@H]4CN)CC3)c(F)c2)C(=O)O1]

Example 19

7-(4-{5-[(5S)-5-(Acetylamino-methyl)-2-oxo-oxazolidin-3-yl]-pyridin-2-yl}-1-piperazin-1-yl)-1-cyclopropyl-6-fluoro-4-oxo-1,4-dihydro-[1,8]naphthyridine-3-carboxylic acid

Example 20

7-(4-{5-[(5S)-5-(Acetylamino-methyl)-2-oxo-oxazolidin-3-yl]-pyridin-2-yl}-piperazin-1-yl)-1-cyclopropyl-6-fluoro-4-oxo-1,4-dihydro-quinoline-3-carboxylic acid

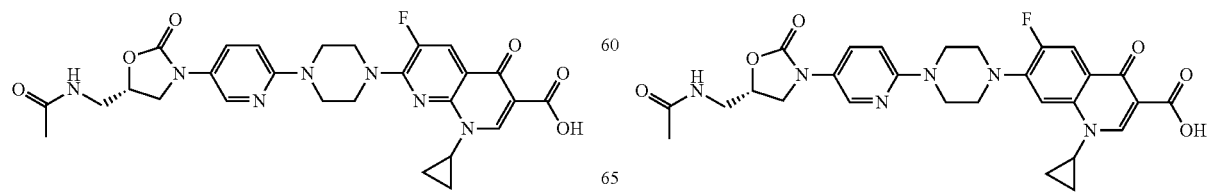

Example 21

7-[(3R)-3-(4-{4[(5S)-5-(Acetylamino-methyl)-2-oxo-oxazolidin-3-yl]-2-fluoro-phenyl}-piperazin-1-yl)-pyrrolidin-1-yl]-1-cyclopropyl-6-fluoro-4-oxo-1,4-dihydro-[1,8]naphthyridine-3-carboxylic acid

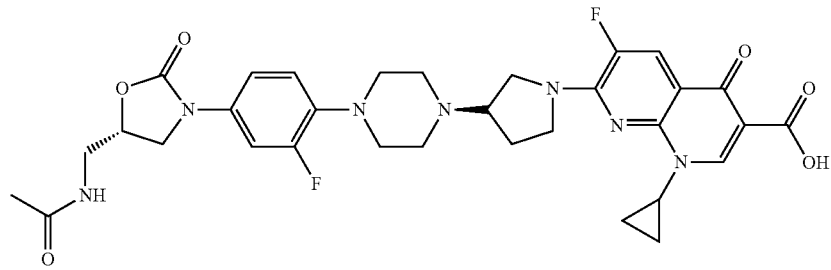

Example 22

1-Cyclopropyl-6-fluoro-7-(4-{2-fluoro-4-[(5R)-5-(methansulfonylamino-methyl)-2-oxo-oxazolidin-3-yl]-phenyl}-piperazin-1-yl)-4-oxo-1,4-dihydro-[1,8]naphthyridine-3-carboxylic acid

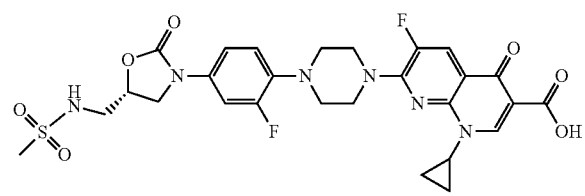 [SMILES: CS(=O)(=O)NC[C@H]1CN(c2ccc(N3CCN(c4nc5c(cc4F)c(=O)c(C(=O)O)cn5C4CC4)CC3)c(F)c2)C(=O)O1]

Example 23

7-(4-{4-[(5S)-5-(Acetylamino-methyl)-2-oxo-oxazolidin-3-yl]-2-fluoro-phenylamino}-piperidin-1-yl)-1-cyclopropyl-6-fluoro-4-oxo-1,4-dihydro-[1,8]naphthyridine-3-carboxylic acid

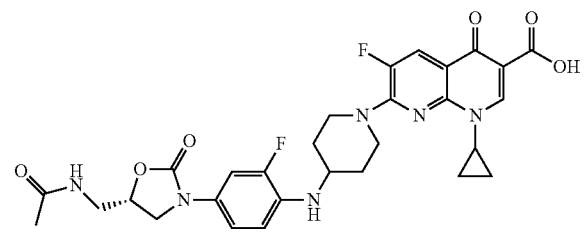 [SMILES: CC(=O)NC[C@H]1CN(c2ccc(NC3CCN(c4nc5c(cc4F)c(=O)c(C(=O)O)cn5C4CC4)CC3)c(F)c2)C(=O)O1]

Example 24

1-Cyclopropyl-6-fluoro-7-(4-{2-fluoro-4-[(5S)-5-(methoxythiocarbonylamino-methyl)-2-oxo-oxazolidin-3-yl]-phenyl}-piperazin-1-yl)-4-oxo-1,4-dihydro-[1,8]-naphthyridine-3-carboxylic acid

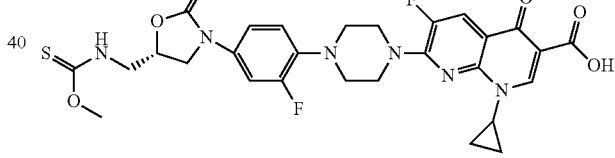

Example 25

1-Cyclopropyl-6-fluoro-7-(4-{2-fluoro-4-((5S)-5-(methylsulfanylthiocarbonylamino-methyl)-2-oxo-oxazolidin-3-yl]-phenyl}-piperazin-1-yl)-4-oxo-1,4-dihydro-[1,8]naphthyridine-3-carboxylic acid

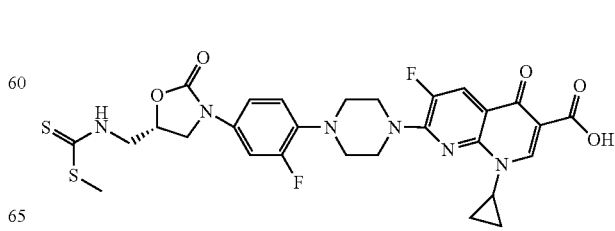

Example 26

1-Cyclopropyl-6-fluoro-{4-[2-fluoro-4-{(5S)-2-oxo-5-thioureidomethyl-oxazolidin-3-yl}-phenyl]-piperazin-1-yl}-4-oxo-1,4-dihydro-[1,8]naphthyridine-3-carboxylic acid

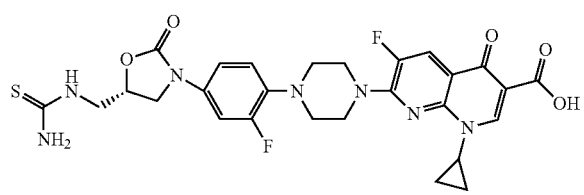 [SMILES: NC(=S)NC[C@H]1CN(c2ccc(N3CCN(c4nc5c(cc4F)c(=O)c(C(=O)O)cn5C4CC4)CC3)c(F)c2)C(=O)O1]

Example 27

7-(4-{4-[5(S)-5-(Acetylamino-methyl)-2-oxo-oxazolidin-3-yl]-2-fluoro-phenoxy}-piperidin-1-yl)-1-cyclopropyl-6-fluoro-4-oxo-1,4-dihydro-[1,8]naphthyridine-3-carboxylic acid

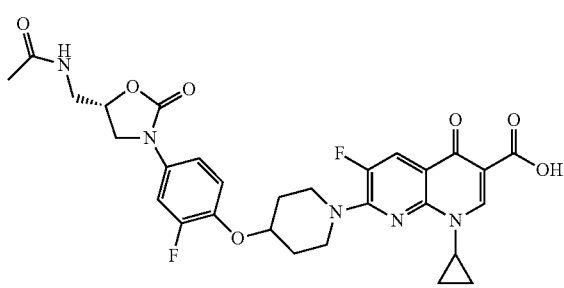 [SMILES: CC(=O)NC[C@H]1CN(c2ccc(OC3CCN(c4nc5c(cc4F)c(=O)c(C(=O)O)cn5C4CC4)CC3)c(F)c2)C(=O)O1]

Example 28

7-(4-{4-[5(S)-5-(Acetylamino-methyl)-2-oxo-oxazolidin-3-yl]-2-fluoro-phenoxy}-piperidin-1-yl)-1-cyclopropyl-6-fluoro-4-oxo-1,4-dihydro-quinoline-3-carboxylic acid

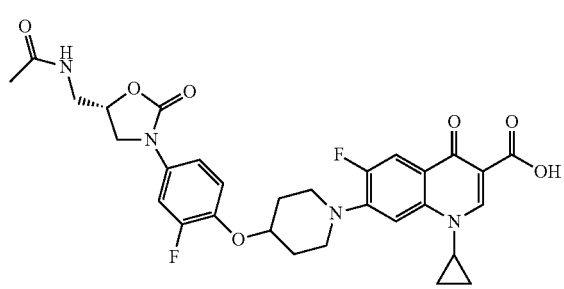 [SMILES: CC(=O)NC[C@H]1CN(c2ccc(OC3CCN(c4cc5c(cc4F)c(=O)c(C(=O)O)cn5C4CC4)CC3)c(F)c2)C(=O)O1]

Example 29

7-(4-{4-[5(S)-5-(Acetylamino-methyl)-2-oxo-oxazolidin-3-yl]-2-fluoro-phenylsulfanyl}-piperidin-1-yl)-1-cyclopropyl-6-fluoro-4-oxo-1,4-dihydro-quinoline-3-carboxylic acid

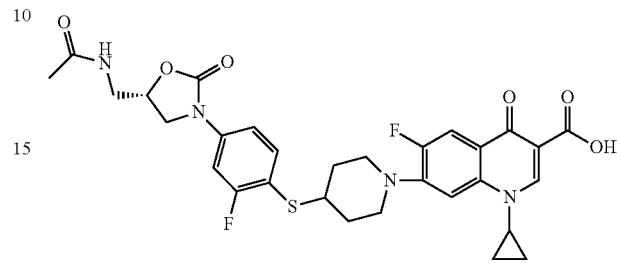

Example 30

7-(4-{4-[5(S)-5(Acetylamino-methyl)-2-oxo-oxazolidin-3-yl]-2-fluoro-phenylsulfanyl}-piperidin-1-yl)-1-cyclopropyl-6-fluoro-4-oxo-1,4-dihydro-[1,8]naphthyridine-3-carboxylic acid

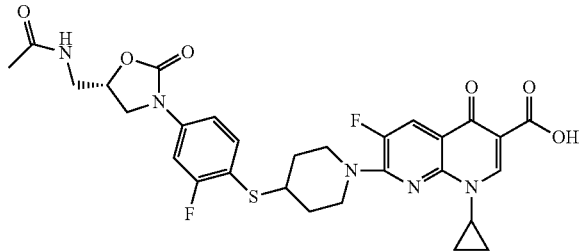 [SMILES: CC(=O)NC[C@H]1CN(c2ccc(SC3CCN(c4cc5c(cc4F)c(=O)c(C(=O)O)cn5C4CC4)CC3)c(F)c2)C(=O)O1]

Example 31

7-(4-{4-[5-(Acetylamino-methyl)-2-oxo-oxazolidin-3-yl]-2-fluoro-benzoyl}-piperazin-1-yl)-1-cyclopropyl-6-fluoro-4-oxo-1,4-dihydro-[1,8]naphthyridine-3-carboxylic acid

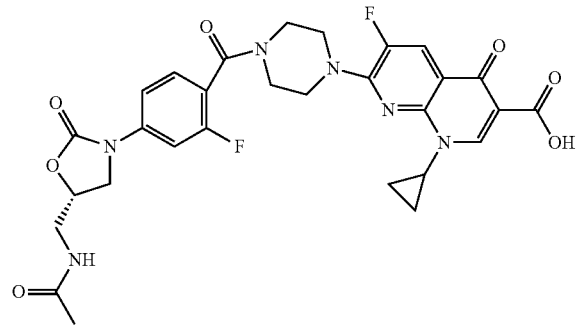 [SMILES: CC(=O)NC[C@H]1CN(c2ccc(C(=O)N3CCN(c4nc5c(cc4F)c(=O)c(C(=O)O)cn5C4CC4)CC3)c(F)c2)C(=O)O1]

Example 32

1-Cyclopropyl-6-fluoro-7-{4-[2-fluoro-4-(5-guanidinomethyl-2-oxo-oxazolidin-3-yl)-phenyl]-piperazin-1-yl}-4-oxo-1,4-dihydro-[1,8]naphthyridine-3-carboxylic acid

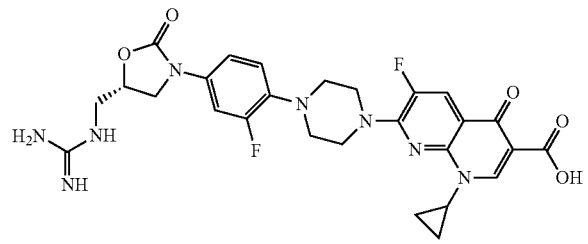 [SMILES: N=C(N)NC[C@H]1CN(c2ccc(N3CCN(c4nc5c(cc4F)c(=O)c(C(=O)O)cn5C4CC4)CC3)c(F)c2)C(=O)O1]

Example 33

7-(4-{4-[5-(Acetylamino-methyl)-2-oxo-oxazolidin-3-yl]-2-fluoro-benzenesulfinyl}-piperidin-1-yl)-1-cyclopropyl-6-fluoro-4-oxo-1,4-dihydro-[1,8]naphthyridine-3-carboxylic acid

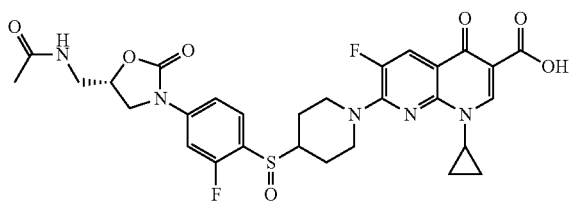 [SMILES: CC(=O)NC[C@H]1CN(c2ccc(S(=O)C3CCN(c4nc5c(cc4F)c(=O)c(C(=O)O)cn5C4CC4)CC3)c(F)c2)C(=O)O1]

Example 34

7-(3-{4-[5-(Acetylamino-methyl)-2-oxo-oxazolidin-3-yl]-2-fluoro-phenoxy}-azetidin-1-yl)-1-cyclopropyl-6-fluoro-4-oxo-1,4-dihydro-[1,8]naphthyridine-3-carboxylic acid

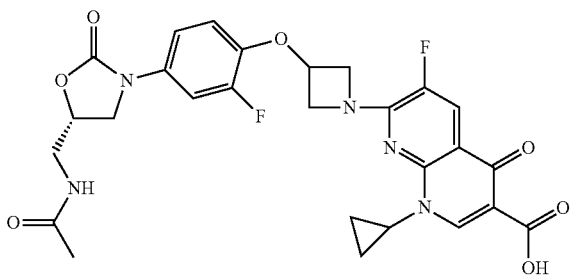 [SMILES: CC(=O)NC[C@H]1CN(c2ccc(OC3CN(c4nc5c(cc4F)c(=O)c(C(=O)O)cn5C4CC4)C3)c(F)c2)C(=O)O1]

A suspension of 100 mg N-{(5S)-3-[4-(Azetidin-3-yloxy)-3-fluoro-phenyl]-2-oxo-oxazolidin-5-yl methyl}-acetamide (MW: 323.32, 0.31 mmol), 73 mg 7-chloro-1-cyclopropyl-6-fluoro-1,4-dihydro-4-oxo-1,8-Naphthyridine-3-carboxylic acid (MW: 282.66, 0.25 mmol), 0.066 ml trimethylchlorosilane (MW: 108.64, d=0.859, 0.51 mmol) and 0.108 ml tri-ethylamine (MW: 101.19, d=0.726, 0.77 mmol) in 2 ml N-methyl-pyrrolidin-2-one was heated under stirring in a micro wave oven at 150° C. for 7 min. The N-methyl-pyrrolidin-2-one was evaporated, the residue was purified by chromatography. Yield: 55 mg, 30%. MS: 570.5 (M+H)$^+$, Method ESI$^+$. Molecular Weight=570

Example 35

7-(3-{4-[5-(Acetylamino-methyl)-2-oxo-oxazolidin-3-yl]-2-fluoro-phenoxy}-pyrrolidin-1-yl)-1-cyclopropyl-6-fluoro-4-oxo-1,4-dihydro-[1,8]naphthyridine-3-carboxylic acid

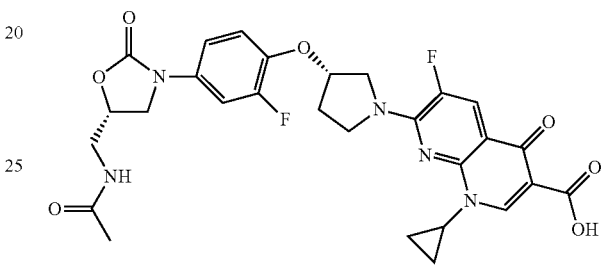

A suspension of 185 mg N-{(5S)-3-[-3-fluoro-4{3-(S)-(pyrrolidin-3-yloxy)}-phenyl]-2-oxo-oxazolidin-5-yl methyl}-acetamide (337.35, 0.55 mmol), 141 mg 7-chloro-1-cyclopropyl-6-fluoro-1,4-dihydro-4-oxo-1,8-Naphthyridine-3-carboxylic acid (MW: 282.66, 0.5 mmol), 0.126 ml trimethylchlorosilane (MW: 108.64, d=0.859, 1 mmol) and 0.209 ml triethylamine (MW: 101.19, d=0.726, 1.5 mmol) in 2 ml N-methyl-pyrrolidin-2-one was heated under stirring in a micro wave oven at 150° C. for 7 min. The N-methyl-pyrrolidin-2-one was evaporated, the residue was purified by chromatography. Molecular Weight=584; Yield: 140 mg, 48%; MS: 584.5 (M+H)$^+$, Method ESI$^+$.

Example 36

7-(3-{4-[5-(Acetylamino-methyl)-2-oxo-oxazolidin-3-yl]-2-fluoro-phenoxy}-pyrrolidin-1-yl)-1-cyclopropyl-6-fluoro-4-oxo-1,4-dihydro-quinoline-3-carboxylic acid

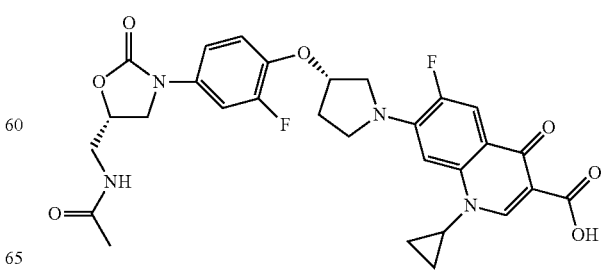

Example 37

7-(4-{4-[5-(Acetylamino-methyl)-2-oxo-oxazolidin-3-yl]-2-fluoro-phenoxymethyl}-piperidin-1-yl)-1-cyclopropyl-6-fluoro-4-oxo-1,4-dihydro-[1,8]naphthyridine-3-carboxylic acid

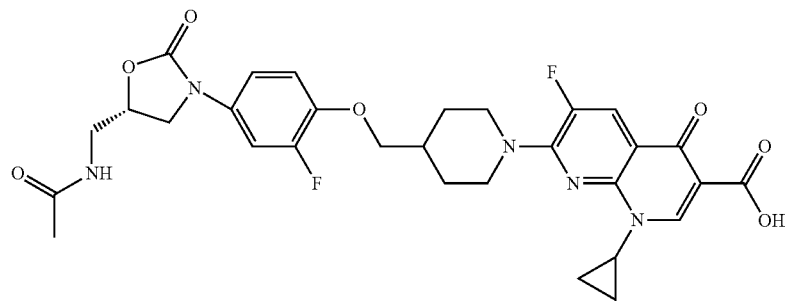 [SMILES: CC(=O)NC[C@H]1CN(c2ccc(OCC3CCN(c4nc5c(cc4F)c(=O)c(C(=O)O)cn5C4CC4)CC3)c(F)c2)C(=O)O1]

Example 38

7-(4-{4-[5-(Acetylamino-methyl)-2-oxo-oxazolidin-3-yl]-2-fluoro-phenoxymethyl}-piperidin-1-yl)-1-cyclopropyl-6-fluoro-4-oxo-1,4-dihydro-quinoline-3-carboxylic acid

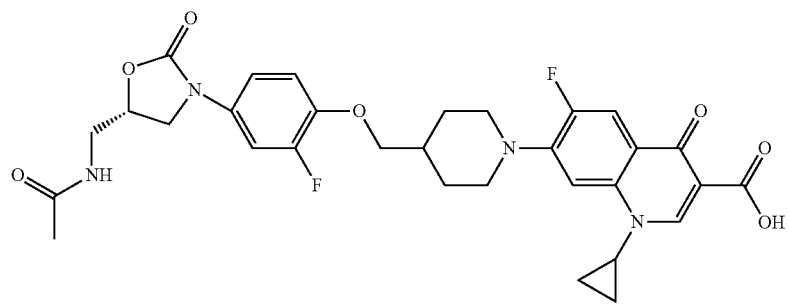 [SMILES: CC(=O)NC[C@H]1CN(c2ccc(OCC3CCN(c4cc5c(cc4F)c(=O)c(C(=O)O)cn5C4CC4)CC3)c(F)c2)C(=O)O1]

Example 39

9-(3-{4-[5-(Acetylamino-methyl)-2-oxo-oxazolidin-3-yl]-2-fluoro-phenoxy}-pyrrolidin-1-yl)-8-fluoro-3-methyl-6-oxo-2,3-dihydro-6H-1-oxa-3a-aza-phenalene-5-carboxylic acid

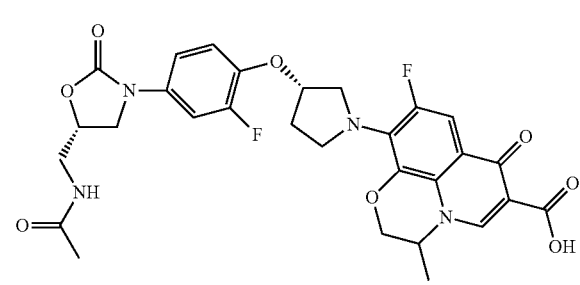 [SMILES: CC(=O)NC[C@H]1CN(c2ccc(O[C@H]3CCN(c4c(F)cc5c(=O)c(C(=O)O)cn6c5c4OCC6C)C3)c(F)c2)C(=O)O1]

Example 40

9-(4-{4-[5-(Acetylamino-methyl)-2-oxo-oxazolidin-3-yl]-2-fluoro-phenoxy}-piperidin-1-yl)-8-fluoro-3-methyl-6-oxo-2,3-dihydro-6H-1-oxa-3a-aza-phenalene-5-carboxylic acid

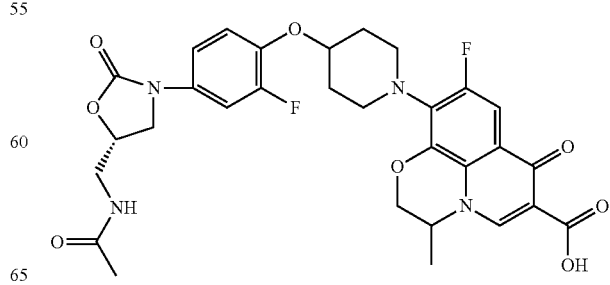

Example 41

9-(3-{4-[5-(Acetylamino-methyl)-2-oxo-oxazolidin-3-yl]-2-fluoro-phenoxy}-piperidin-1-yl)-8-fluoro-3-methyl-6-oxo-2,3-dihydro-6H-1-oxa-3a-aza-phenalene-5-carboxylic acid

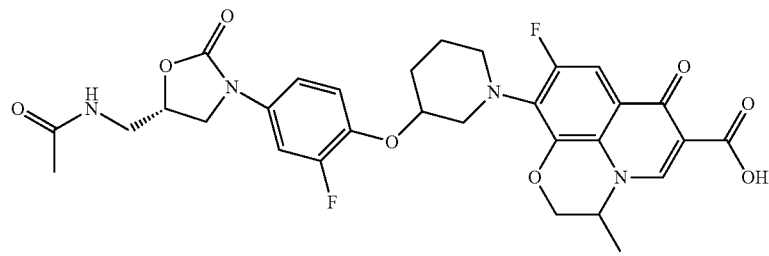 [SMILES: CC(=O)NC[C@H]1CN(c2ccc(OC3CCCN(c4c(F)cc5c(=O)c(C(=O)O)cn6c5c4OCC6C)C3)c(F)c2)C(=O)O1]

Example 42

7-(3-{4-[5-(Acetylamino-methyl)-2-oxo-oxazolidin-3-yl]-2-fluoro-phenoxy}-pyrrolidin-1-yl)-1-cyclopropyl-6-fluoro-4-oxo-1,4-dihydro-[1,8]naphthyridine-3-carboxylic acid

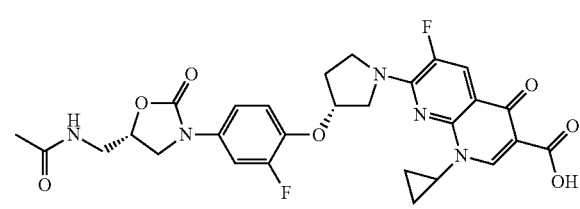 [SMILES: CC(=O)NC[C@H]1CN(c2ccc(O[C@@H]3CCN(c4nc5c(cc4F)c(=O)c(C(=O)O)cn5C4CC4)C3)c(F)c2)C(=O)O1]

Example 43

9-(3-{4-[5-(Acetylamino-methyl)-2-oxo-oxazolidin-3-yl]-2-fluoro-phenoxy}-pyrrolidin-1-yl)-8-fluoro-3-methyl-6-oxo-2,3-dihydro-6H-1-oxa-3a-aza-phenalene-5-carboxylic acid

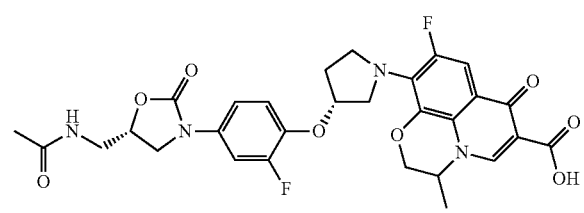 [SMILES: CC(=O)NC[C@H]1CN(c2ccc(O[C@@H]3CCN(c4c(F)cc5c(=O)c(C(=O)O)cn6c5c4OCC6C)C3)c(F)c2)C(=O)O1]

Example 44

9-(3-{4-[5-(Acetylamino-methyl)-2-oxo-oxazolidin-3-yl]-2-fluoro-phenoxy}-azetidin-1-yl)-8-fluoro-3-methyl-6-oxo-2,3-dihydro-6H-1-oxa-3a-aza-phenalene-5-carboxylic acid

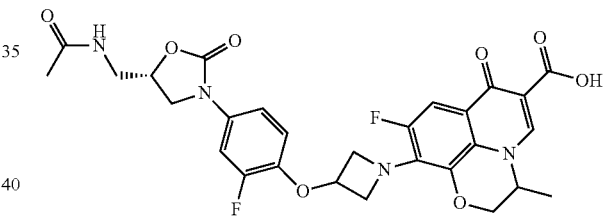

Example 45

9-(4-{4-[5-(Acetylamino-methyl)-2-oxo-oxazolidin-3-yl]-2-fluoro-phenylsulfanyl}-piperidin-1-yl)-8-fluoro-3-methyl-6-oxo-2,3-dihydro-6H-1-oxa-3a-aza-phenalene-5-carboxylic acid

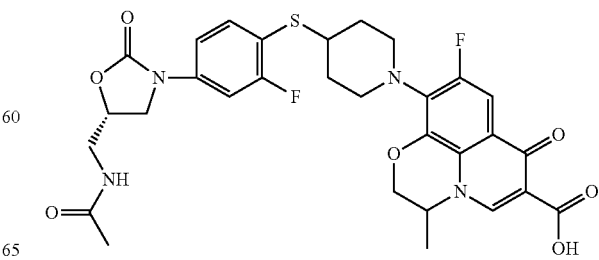

Example 46

7-(3-{4-[5-(Acetylamino-methyl)-2-oxo-oxazolidin-3-yl]-2-fluoro-phenoxymethyl}-pyrrolidin-1-yl)-1-cyclopropyl-6-fluoro-4-oxo-1,4-dihydro-[1,8]naphthyridine-3-carboxylic acid

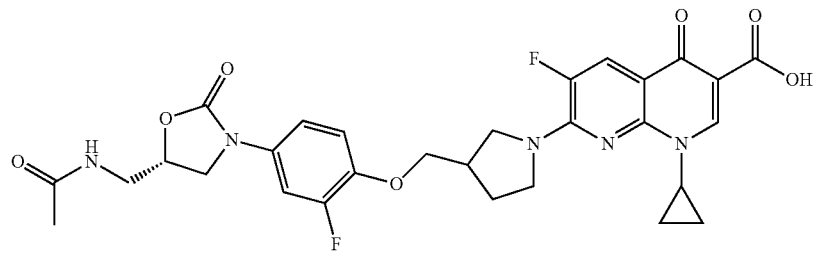 [SMILES: CC(=O)NC[C@H]1CN(c2ccc(OCC3CCN(c4nc5c(cc4F)c(=O)c(C(=O)O)cn5C4CC4)C3)c(F)c2)C(=O)O1]

A suspension of 179 mg N-{(5S)-3-[3-fluoro-4-[3-(RS)-(pyrrolidin-3-ylmethoxy)]-phenyl]-2-oxo-oxazolidin-5-yl methyl}-acetamide (MW: 351.38, 0.55 mmol), 141 mg 7-chloro-1-cyclopropyl-6-fluoro-1,4-dihydro-4-oxo-1,8-Naphthyridine-3-carboxylic acid (MW: 282.66, 0.5 mmol), 0.128 ml trimethylchlorosilane (MW: 108.64, d=0.859, 1.0 mmol) and 0.200 ml triethylamine (MW: 101.19, d=0.726, 1.5 mmol) in 2 ml N-methyl-pyrrolidin-2-one was heated under stirring in a micro wave oven at 150° C. for 7 min. The N-methyl-pyrrolidin-2-one was evaporated, the residue was purified by chromatography. Yield: 241 mg, 81%. MS: 598.5 (M+H)$^+$, Method ESI$^+$. Molecular Weight=598.

Example 47

9-(3-{4-[5-(Acetylamino-methyl)-2-oxo-oxazolidin-3-yl]-2-fluoro-phenoxymethyl}-pyrrolidin-1-yl)-8-fluoro-3-methyl-6-oxo-2,3-dihydro-6H-1-oxa-3a-aza-phenalene-5-carboxylic acid

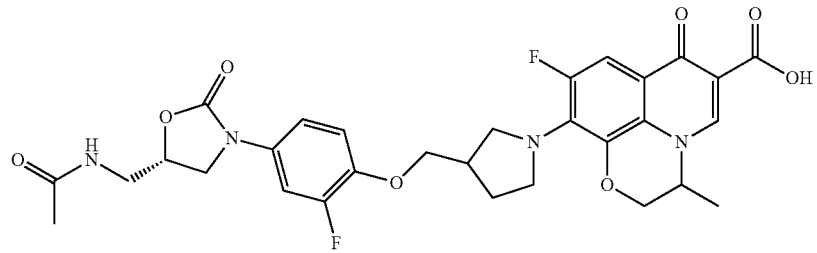 [SMILES: CC(=O)NC[C@H]1CN(c2ccc(OCC3CCN(c4c(F)cc5c(=O)c(C(=O)O)cn6c5c4OCC6C)C3)c(F)c2)C(=O)O1]

A suspension of 179 mg N-{(5S)-3-[3-fluoro-4-[3-(RS)-(pyrrolidin-3-ylmethoxy)]-phenyl]-2-oxo-oxazolidin-5-yl methyl}-acetamide (MW: 351.38, 0.55 mmol), 140 mg 9-10-difluoro-2,3-dihydro-3-methyl-7-oxo-7H-pyrido[1,2,3-de]-1,4-benzoxazine-6-carboxilic acid (MW: 281.21, 0.5 mmol), 0.128 ml trimethylchlorosilane (MW: 108.64, d=0.859, 1.0 mmol) and 112 mg 1,4-diazabicyclo[2.2.2]octane (MW: 112.18, 1.0 mmol) in 2 ml N-methyl-pyrrolidin-2-one was heated under stirring in a micro wave oven at 150° C. for 7 min. The N-methyl-pyrrolidin-2-one was evaporated, the residue was purified by crystallisation. Yield: 161 mg, 52%. MS: 613.5 (M+H)$^+$, Method ESI. Molecular Weight=613.

Example 48

9-(4-{4-[5-(Acetylamino-methyl)-2-oxo-oxazolidin-3-yl]-2-fluoro-phenoxymethyl}-piperidin-1-yl)-8-fluoro-3-methyl-6-oxo-2,3-dihydro-6H-1-oxa-3a-aza-phenalene-5-carboxylic acid

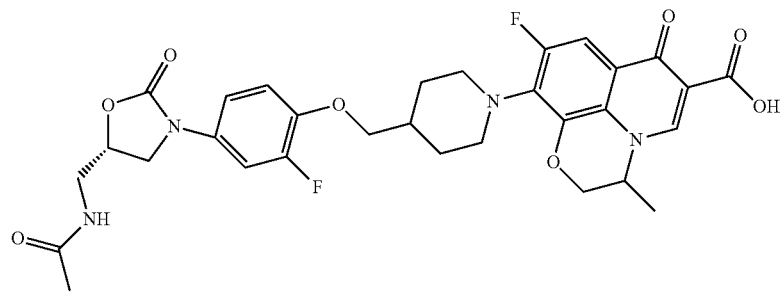 [SMILES: CC(=O)NC[C@H]1CN(c2ccc(OCC3CCN(c4c(F)cc5c(=O)c(C(=O)O)cn6c5c4OCC6C)CC3)c(F)c2)C(=O)O1]

Example 49

7-[4-(3-{4-[5-(Acetylamino-methyl)-2-oxo-oxazolidin-3-yl]-2-fluoro-phenoxy}-propyl)-piperidin-1-yl]-1-cyclopropyl-6-fluoro-4-oxo-1,4-dihydro-[1,8]naphthyridine-3-carboxylic acid

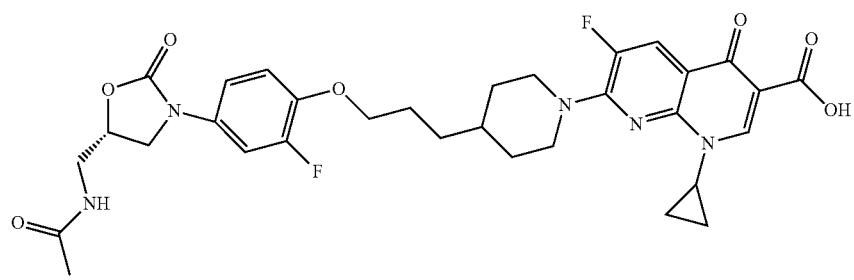 [SMILES: CC(=O)NC[C@H]1CN(c2ccc(OCCCC3CCN(c4nc5c(cc4F)c(=O)c(C(=O)O)cn5C4CC4)CC3)c(F)c2)C(=O)O1]

Example 50

9-[4-(3-{4-[5-(Acetylamino-methyl)-2-oxo-oxazolidin-3-yl]-2-fluoro-phenoxy}-propyl)-piperidin-1-yl]-8-fluoro-3-methyl-6-oxo-2,3-dihydro-6H-1-oxa-3a-aza-phenalene-5-carboxylic acid

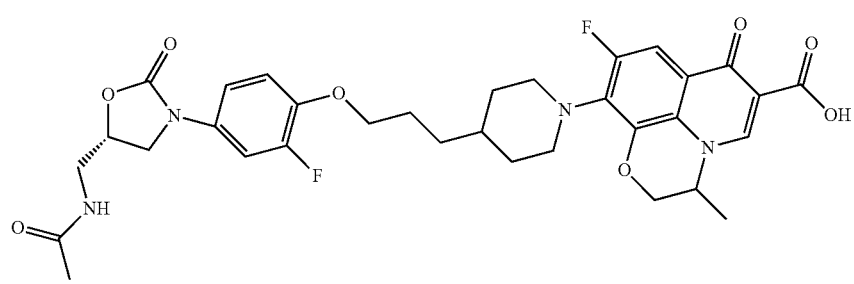 [SMILES: CC(=O)NC[C@H]1CN(c2ccc(OCCCC3CCN(c4c(F)cc5c(=O)c(C(=O)O)cn6c5c4OCC6C)CC3)c(F)c2)C(=O)O1]

Example 51

7-(4-{4-[5-(Acetylamino-methyl)-2-oxo-oxazolidin-3-yl]-2-fluoro-phenoxy}-azepan-1-yl)-1-cyclopropyl-6-fluoro-4-oxo-1,4-dihydro-[1,8]naphthyridine-3-carboxylic acid

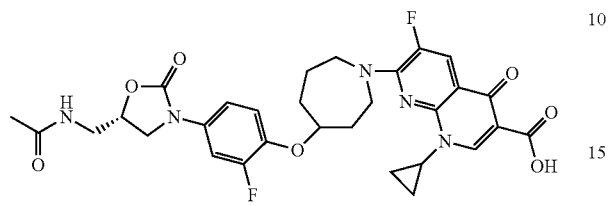

Example 52

9-(4-{4-[5-(Acetylamino-methyl)-2-oxo-oxazolidin-3-yl]-2-fluoro-phenoxy}-azepan-1-yl)-8-fluoro-3-methyl-6-oxo-2,3-dihydro-6H-1-oxa-3a-aza-phenalene-5-carboxylic acid

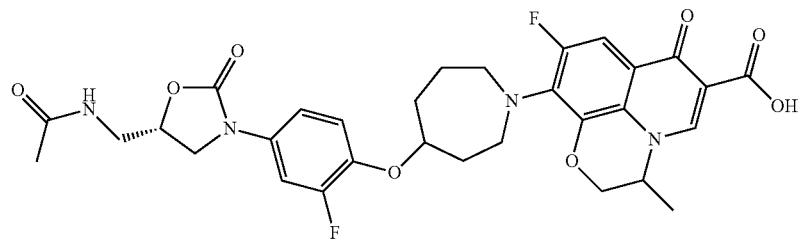 [SMILES: CC(=O)NC[C@H]1CN(c2ccc(OC3CCCN(c4c(F)cc5c(=O)c(C(=O)O)cn6c5c4OCC6C)CC3)c(F)c2)C(=O)O1]

Example 53

7-[4-(2-{4-[(5S)-(Acetylamino-methyl)-2-oxo-oxazolidin-3-yl]-2-fluoro-phenoxy}-ethyl)-piperidin-1-yl]-1-cyclopropyl-6-fluoro-4-oxo-1,4-dihydro-[1,8]naphthyridine-3-carboxylic acid

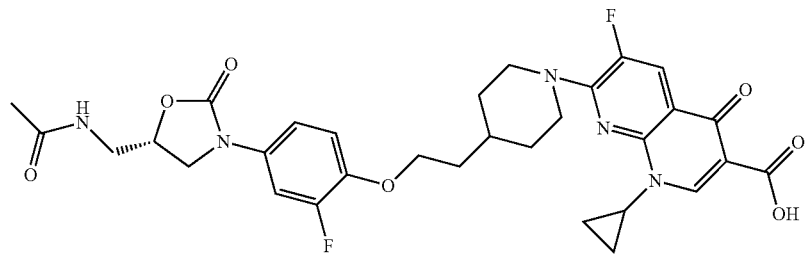 [SMILES: CC(=O)NC[C@H]1CN(c2ccc(OCCC3CCN(c4nc5c(cc4F)c(=O)c(C(=O)O)cn5C4CC4)CC3)c(F)c2)C(=O)O1]

A suspension of 100 mg N-{(5S)-3-[3-fluoro-4-[4-(piperazin-4-yl-ethoxy)]-phenyl]-2-oxo-oxazolidin-5-ylmethyl}-acetamide (MW: 379.43, 0.263 mmol), 68 mg 7-chloro-1-cyclopropyl-6-fluoro-1,4-dihydro-4-oxo-1,8-Naphthyridine-3-carboxylic acid (MW: 282.66, 0.239 mmol), 0.060 ml trimethylchlorosilane (MW: 108.64, d=0.859, 0.47 mmol) and 0.1 ml triethylamine (MW: 101.19, d=0.726, 0.71 mmol) in 2 ml N-methyl-pyrrolidin-2-one was heated under stirring in a micro wave oven at 150° C. for 7 min. The N-methyl-pyrrolidin-2-one was evaporated, the residue was purified by chromatography. Yield: 30 mg, 20%. MS: 626.5 (M+H)$^+$, Method ESI$^+$. Molecular Weight=626

Example 54

9-[4-(2-{4-[5-(Acetylamino-methyl)-2-oxo-oxazolidin-3-yl]-2-fluoro-phenoxy}-ethyl)-piperidin-1-yl]-8-fluoro-3-methyl-6-oxo-2,3-dihydro-6H-1-oxa-3a-aza-phenalene-5-carboxylic acid

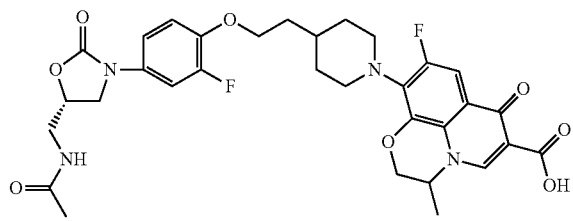 [SMILES: CC(=O)NC[C@H]1CN(c2ccc(OCCC3CCN(c4c(F)cc5c(=O)c(C(=O)O)cn6c5c4OCC6C)CC3)c(F)c2)C(=O)O1]

Example 55

7-[3(R,S)-(2-{4-[(5S)-(Acetylamino-methyl)-2-oxo-oxazolidin-3-yl]-2-fluoro-phenoxy}-ethyl)-pyrrolidin-1-yl]-1-cyclopropyl-6-fluoro-4-oxo-1,4-dihydro-[1,8]naphthyridine-3-carboxylic acid

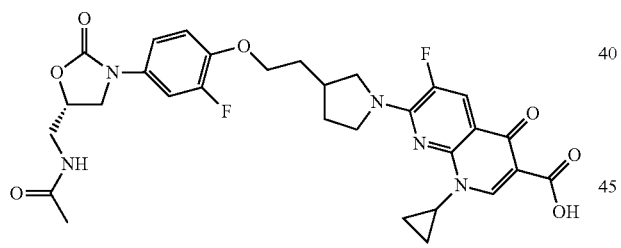

A suspension of 120 mg N-{(5S)-3-[3-fluoro-4-[4(R,S)-4-(piperazin-4-yl-ethoxy)]-phenyl]-2-oxo-oxazolidin-5-ylm-ethyl}-acetamide (MW: 365.40, 0.33 mmol), 85 mg 7-chloro-1-cyclopropyl-6-fluoro-1,4-dihydro-4-oxo-1,8-Naphthyridine-3-carboxylic acid (MW: 282.66, 0.3 mmol), 0.075 ml trimethylchlorosilane (MW: 108.64, d=0.859, 0.6 mmol) and 0.127 ml triethylamine (MW: 101.19, d=0.726, 0.9 mmol) in 3 ml N-methyl-pyrrolidin-2-one was heated under stirring in a micro wave oven at 150° C. for 7 min. The N-methyl-pyrrolidin-2-one was evaporated, and the residue dissolved in dichloromethane. The organic layer was washed with water and brine, dried over Mg sulfate, filtered and the filtrate evaporated. The residue was digested in ethyl acetate, the resulting colourless solid was filtered and dried. Yield: 159 mg, 86%. Molecular Weight 612.

Example 56

9-[3-(2-{4-[5-(Acetylamino-methyl)-2-oxo-oxazolidin-3-yl]-2-fluoro-phenoxy}-ethyl)-pyrrolidin-1-yl]-8-fluoro-3-methyl-6-oxo-2,3-dihydro-6H-1-oxa-3a-aza-phenalene-5-carboxylic acid

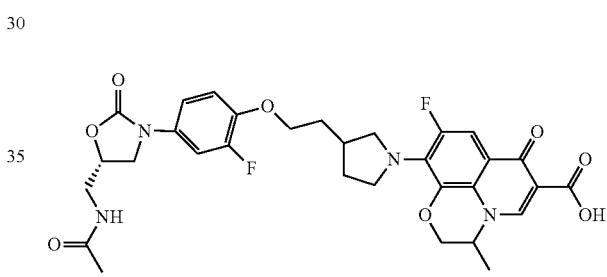

Example 57

7-(3-{4-[5-(Acetylamino-methyl)-2-oxo-oxazolidin-3-yl]-2-fluoro-phenoxymethyl}-pyrrolidin-1-yl)-1-cyclopropyl-6-fluoro-4-oxo-1,4-dihydro-quinoline-3-carboxylic acid

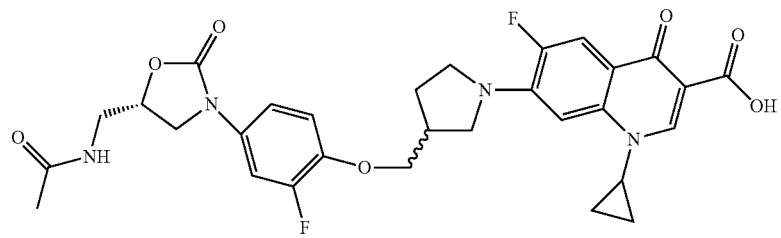 [SMILES: CC(=O)NC[C@H]1CN(c2ccc(OCC3CCN(c4cc5c(cc4F)c(=O)c(C(=O)O)cn5C4CC4)C3)c(F)c2)C(=O)O1]

A suspension of 176 mg N-{(5S)-3-[3-fluoro-4-[3-(RS)-(pyrrolidin-3-ylmethoxy)]-phenyl]-2-oxo-oxazolidin-5-yl methyl}-acetamide (MW: 351.38, 0.5 mmol), 205 mg 7-chloro-6-fluoro-1-cyclopropyl-4-oxo-1,4-dihydroquinoline-3-carboxylato-boron diacetate (MW: 409.56, 0.5 mmol), and 0.341 ml N-ethyldiisopropylamine (MW: 129.25, d=0.755, 2 mmol) in 2 ml N-methyl-pyrrolidin-2-one was heated under stirring in a micro wave oven at 150° C. for 7 min. The N-methyl-pyrrolidin-2-one was evaporated, the residue was purified by chromatography and crystallisation from ethanol. Yield: 120 mg, 40%. MS: 597.5 (M+H)$^+$, Method ESI$^+$. Molecular Weight=597.

Example 58

7-[3-(2-{4-[5-(Acetylamino-methyl)-2-oxo-oxazolidin-3-yl]-2-fluoro-phenoxy}-ethyl)-pyrrolidin-1-yl]-1-cyclopropyl-6-fluoro-4-oxo-1,4-dihydro-quinoline-3-carboxylic acid

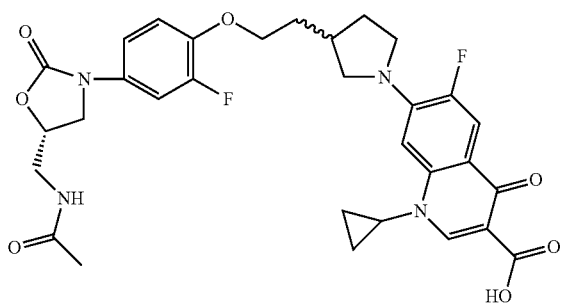 [SMILES: CC(=O)NC[C@H]1CN(c2ccc(OCCC3CCN(c4cc5c(cc4F)c(=O)c(C(=O)O)cn5C4CC4)C3)c(F)c2)C(=O)O1]

Example 59

7-(3-{4-[5-(Acetylamino-methyl)-2-oxo-oxazolidin-3-yl]-2-fluoro-phenoxymethyl}-pyrrolidin-1-yl)-1-cyclopropyl-8-methoxy-4-oxo-1,4-dihydro-quinoline-3-carboxylic acid

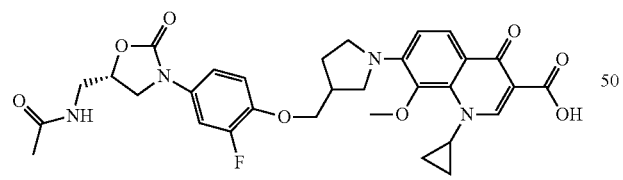

A suspension of 100 mg N-{(5S)-3-[3-fluoro-4-[3-(RS)-(pyrrolidin-3-ylmethoxy)]-phenyl]-2-oxo-oxazolidin-5-yl methyl}-acetamide (MW: 351.38, 0.284 mmol), 115 mg 1-cyclopropyl-7-fluoro-8-methoxy-4-oxo-1,4-dihydro-quinoline-3-carboxylatoboron diacetate (MW: 405.14, 0.284 mmol) and 0.097 ml N-ethyldiisopropylamine (MW: 129.25, d=0.755, 0.57 mmol) in 2 ml N-methyl-pyrrolidin-2-one was heated under stirring in a micro wave oven at 150° C. for 7 min. The N-methyl-pyrrolidin-2-one was evaporated, the residue was purified by chromatography and crystallisation from ethanol. Yield: 40 mg, 23%. MS: 609.5 (M+H)$^+$, Method ESI$^+$. Molecular Weight=609.

Example 60

7-(3-{4-[5-(Acetylamino-methyl)-2-oxo-oxazolidin-3-yl]-2-fluoro-phenoxy}-pyrrolidin-1-yl)-6-fluoro-1-(4-hydroxy-phenyl)-4-oxo-1,4-dihydro-quinoline-3-carboxylic acid

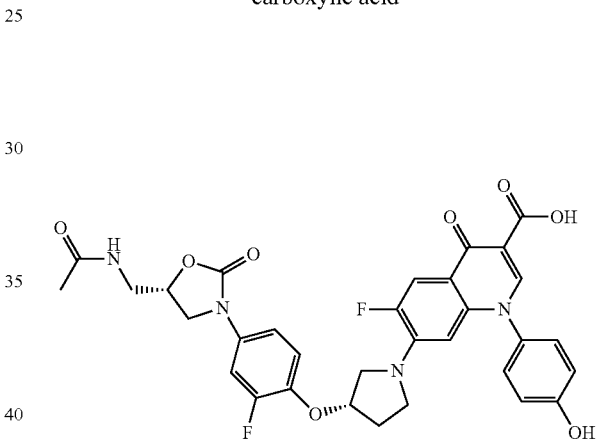

Example 61

7-(3-{4-[5-(Acetylamino-methyl)-2-oxo-oxazolidin-3-yl]-2-fluoro-phenoxymethyl}-pyrrolidin-1-yl)-1-cyclopropyl-6-fluoro-8-methoxy-4-oxo-1,4-dihydro-quinoline-3-carboxylic acid

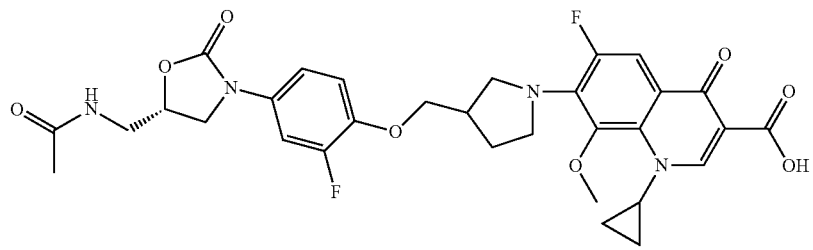 [SMILES: COc1c(N2CCC(COc3ccc(N4C[C@H](CNC(C)=O)OC4=O)cc3F)C2)c(F)cc2c(=O)c(C(=O)O)cn(C3CC3)c12]

Example 62

7-[4-(2-{4-[5-(Acetylamino-methyl)-2-oxo-oxazolidin-3-yl]-phenyl}-2-oxo-ethyl)-piperazin-1-yl]-1-cyclopropyl-6-fluoro-4-oxo-1,4-dihydro-quinoline-3-carboxylic acid

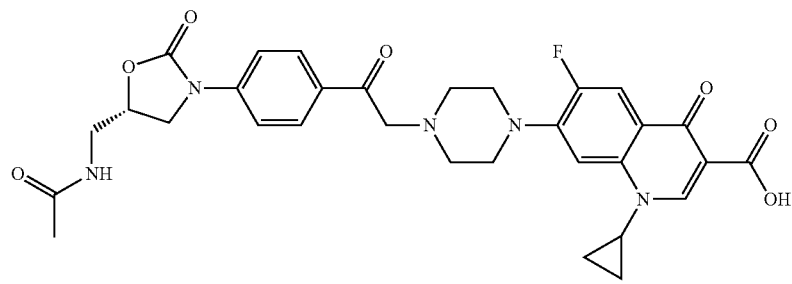 [SMILES: CC(=O)NC[C@H]1CN(c2ccc(C(=O)CN3CCN(c4cc5c(cc4F)c(=O)c(C(=O)O)cn5C4CC4)CC3)cc2)C(=O)O1]

Example 63

7-(3(S)-{4-[5(S)-(Acetylamino-methyl)-2-oxo-oxazolidin-3-yl]-2-fluoro-phenoxymethyl}-pyrrolidin-1-yl)-1-cyclopropyl-6-fluoro-4-oxo-1,4-dihydro-[1,8]naphthyridine-3-carboxylic acid

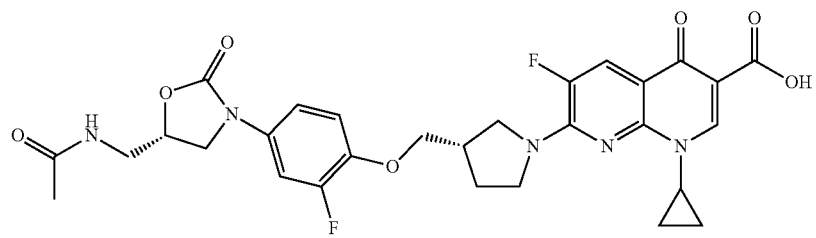 [SMILES: CC(=O)NC[C@H]1CN(c2ccc(OC[C@H]3CCN(c4nc5c(cc4F)c(=O)c(C(=O)O)cn5C4CC4)C3)c(F)c2)C(=O)O1]

A suspension of 737 mg N-{(5S)-3-[3-fluoro-4-[3-(S)-(pyrrolidin-3-ylmethoxy)]-phenyl]-2-oxo-oxazolidin-5-yl methyl}-acetamide (MW: 351.38, 2.1 mmol), 566 mg 7-chloro-1-cyclopropyl-6-fluoro-1,4-dihydro-4-oxo-1,8-Naphthyridine-3-carboxylic acid (MW: 282.66, 2 mmol), 0.505 ml trimethyl-chlorosilane (MW: 108.64, d=0.859, 4 mmol) and 0.840 ml triethylamine (MW: 101.19, d=0.726, 6 mmol) in 15 ml N-methyl-pyrrolidin-2-one was heated under stirring at 150° C. for 2 hrs. The N-methyl-pyrrolidin-2-one was evaporated, and the residue dissolved in dichloromethane. The organic layer was washed with water and brine, dried over Mg sulfate, filtered and the filtrate evaporated. The residue was purified by crystallisation from an ethanol and dichloromethane mixture. Yield: 972 mg, 81%. MS: 598.5 (M+H)$^+$, Method ESI$^+$. Molecular Weight 598.

Example 64

7-(3(R)-{4-[5(S)-(Acetylamino-methyl)-2-oxo-oxazolidin-3-yl]-2-fluoro-phenoxymethyl}-pyrrolidin-1-yl)-1-cyclopropyl-6-fluoro-4-oxo-1,4-dihydro-quinoline-3-carboxylic acid

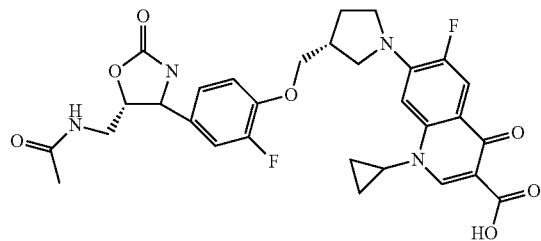 [SMILES: CC(=O)NC[C@@H]1OC(=O)NC1c1ccc(OC[C@@H]2CCN(c3cc4c(cc3F)c(=O)c(C(=O)O)cn4C3CC3)C2)c(F)c1]

A suspension of 1.228 g N-{(5S)-3-[3-fluoro-4-[3-(R)-(pyrrolidin-3-ylmethoxy)]-phenyl]-2-oxo-oxazolidin-5-yl methyl}-acetamide (MW: 351.38, 3 mmol), 1.054 g 7-chloro-6-fluoro-1-cyclopropyl-4-oxo-1,4-dihydroquinoline-3-carboxylato-boron diacetate (MW: 409.56, 3 mmol), and 2 ml N-ethyl-diisopropylamine (MW: 129.25, d=0.755, 12 mmol) in 30 ml N-methyl-pyrrolidin-2-one was heated under stirring at 150° C. for 2 hrs. The N-methyl-pyrrolidin-2-one was evaporated, and the residue dissolved in dichloromethane. The organic layer was washed with 0.1N HCl and with brine, dried over Mg sulfate, filtered and the filtrate evaporated to dryness. The residue was digested in warm ethyl acetate, the crystals filtered (DC1). The solid was crystallised from ethanol. Yield: 728 mg, 41%. MS: 597.5 (M+H)$^+$, Method ESI$^+$. Molecular Weight 597.

Example 65

7-[4-(2-{4-[5-(Acetylamino-methyl)-2-oxo-oxazolidin-3-yl]-2-fluoro-phenoxy}-ethylidene)-piperidin-1-yl]-1-cyclopropyl-6-fluoro-4-oxo-1,4-dihydro-[1,8]-naphthyridine-3-carboxylic acid

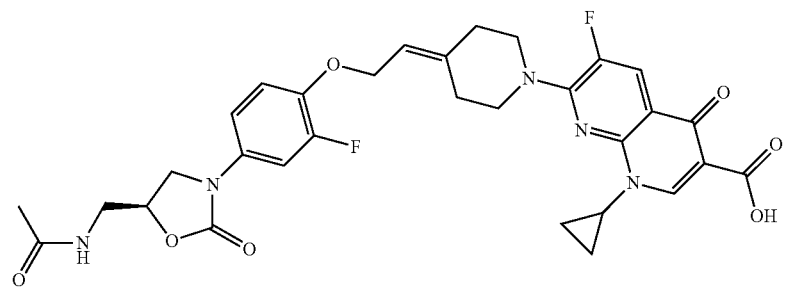 [SMILES: CC(=O)NC[C@H]1CN(c2ccc(OCC=C3CCN(c4nc5c(cc4F)c(=O)c(C(=O)O)cn5C4CC4)CC3)c(F)c2)C(=O)O1]

Example 66

7-(3-{4-[5-(Acetylamino-methyl)-2-oxo-oxazolidin-3-yl]-2-fluoro-phenoxymethyl}-azetidin-1-yl)-1-cyclopropyl-6-fluoro-4-oxo-1,4-dihydro-[1,8]naphthyridine-3-carboxylic acid

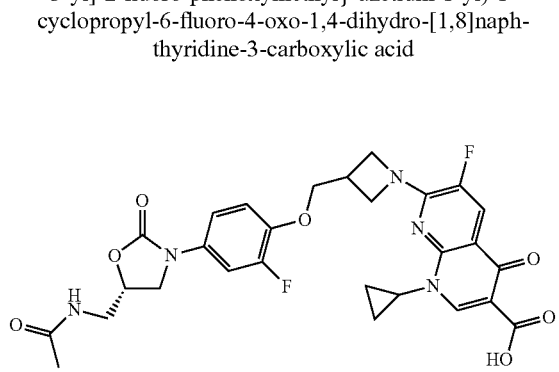

A suspension of 179 mg N-{(5S)-3-[4-(Azetidin-3-yl-methoxy)-3-fluoro-phenyl]-2-oxo-oxazolidin-5-yl methyl}-acetamide (MW: 337.35, 0.31 mmol), 100 mg 7-chloro-1-cyclopropyl-6-fluoro-1,4-dihydro-4-oxo-1,8-Naphthyridine-3-carboxylic acid (MW: 282.66, 0.25 mmol), 0.134 ml trimethylchlorosilane (MW: 108.64, d=0.859, 1.059 mmol) and 0.197 ml triethylamine (MW: 101.19, d=0.726, 1.41 mmol) in 2 ml N-methyl-pyrrolidin-2-one was heated under stirring in a micro wave oven at 150° C. for 7 min. The N-methyl-pyrrolidin-2-one was evaporated, the residue was purified by chromatography. Yield: 82 mg, 40%. MS: 583.5 (M+H)$^+$, Method ESI$^+$. Molecular Weight=584

Example 67

7-(2-{4-[5-(Acetylamino-methyl)-2-oxo-oxazolidin-3-yl]-2-fluoro-phenoxymethyl}-1-oxa-6-aza-spiro[2.5]oct-6-yl)-1-cyclopropyl-6-fluoro-4-oxo-1,4-dihydro-[1,8]naphthyridine-3-carboxylic acid

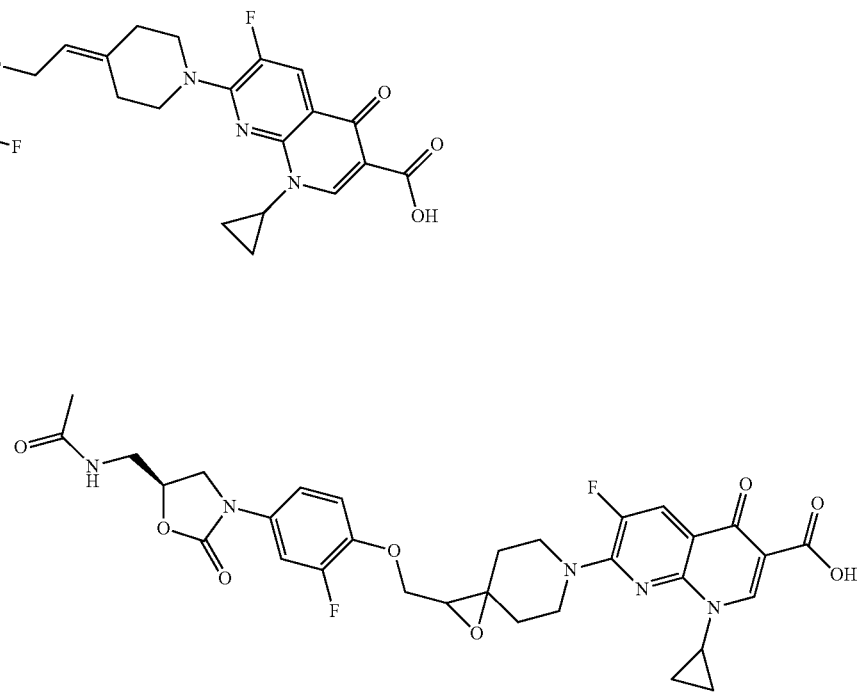

Example 68

7-(3-{4-[5-(Acetylamino-methyl)-2-oxo-oxazolidin-3-yl]-2-fluoro-phenoxy}-4-methoxy-pyrrolidin-1-yl)-1-cyclo-propyl-6-fluoro-4-oxo-1,4-dihydro-[1,8]-naphthyridine-3-carboxylic acid

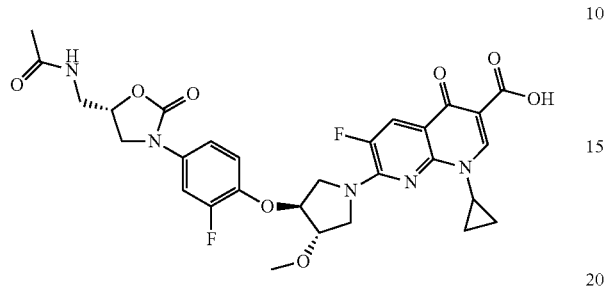

Example 69

7-(3(R)-{4-[5(S)-(Acetylamino-methyl)-2-oxo-oxazolidin-3-yl]-2-fluoro-phenoxymethyl}-pyrrolidin-1-yl)-1-cyclopropyl-6-fluoro-4-oxo-1,4-dihydro-[1,8]naphthyridine-3-carboxylic acid

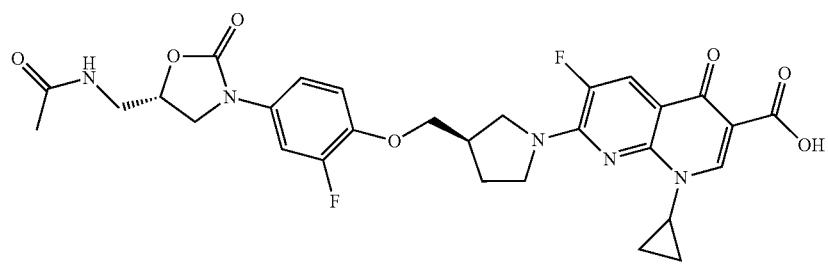 [SMILES: CC(=O)NC[C@H]1CN(c2ccc(OC[C@@H]3CCN(c4nc5c(cc4F)c(=O)c(C(=O)O)cn5C4CC4)C3)c(F)c2)C(=O)O1]

A suspension of 150 mg N-{(5S)-3-[3-fluoro-4-[3-(R)-(pyrrolidin-3-ylmethoxy)]-phenyl]-2-oxo-oxazolidin-5-yl methyl}-acetamide (MW: 351.38, 0.42 mmol), 100 mg 7-chloro-1-cyclopropyl-6-fluoro-1,4-dihydro-4-oxo-1,8-Naphthyridine-3-carboxylic acid (MW: 282.66, 0.35 mmol), 0.147 ml trimethyl-chlorosilane (MW: 108.64, d=0.859, 1.16 mmol) and 0.216 ml triethylamine (MW: 101.19, d=0.726, 1.54 mmol) in 2 ml N-methyl-pyrrolidin-2-one was heated under stirring in a micro wave oven at 150° C. for 7 min. The N-methyl-pyrrolidin-2-one was evaporated, the residue was purified by chromatography. Yield: 150 mg, 60%. MS: 598.5 (M+H)$^+$, Method ESI$^+$. Molecular Weight 598.

Example 70

7-[4-(2-{4-[5-(Acetylamino-methyl)-2-oxo-oxazolidin-3-yl]-2-fluoro-phenoxy}-ethyl)-piperidin-1-yl]-1-cyclopropyl-6-fluoro-4-oxo-1,4-dihydro-quinoline-3-carboxylic

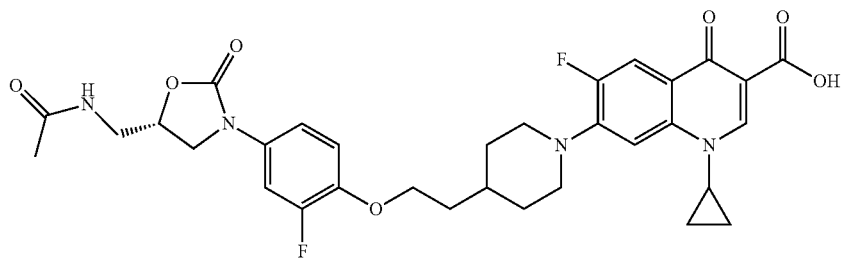 [SMILES: CC(=O)NC[C@H]1CN(c2ccc(OCCC3CCN(c4cc5c(cc4F)c(=O)c(C(=O)O)cn5C4CC4)CC3)c(F)c2)C(=O)O1]

Example 71

7-(3-{4-[5-(Acetylamino-methyl)-2-oxo-oxazolidin-3-yl]-2-fluoro-phenoxy}-piperidin-1-yl)-1-cyclopropyl-6-fluoro-4-oxo-1,4-dihydro-[1,8]naphthyridine-3-carboxylic acid

A suspension of 100 mg N-{(5S)-3-[3-fluoro-4-{3(RS)-piperidin-3-yloxy}-phenyl]-2-oxo-oxazolidin-5-yl methyl}-acetamide (MW: 351.38, 0.28 mmol), 67 mg 7-chloro-1-cyclopropyl-6-fluoro-1,4-dihydro-4-oxo-1,8-Naphthyridine-3-carboxylic acid (MW: 282.66, 0.23 mmol), 0.060 ml trimethylchlorosilane (MW: 108.64, d=0.859, 0.47 mmol) and 0.10 ml triethylamine (MW: 101.19, d=0.726, 0.71 mmol) in 2 ml N-methyl-pyrrolidin-2-one was heated under stirring in a micro wave oven at 150° C. for 7 min. The N-methyl-pyrrolidin-2-one was evaporated, the residue was purified by chromatography. Yield: 60 mg, 42%. MS: 598.5 (M+H)$^+$, Method ESI$^+$.

Example 72

7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-[1,8]naphthyridine-3-carboxylic acid

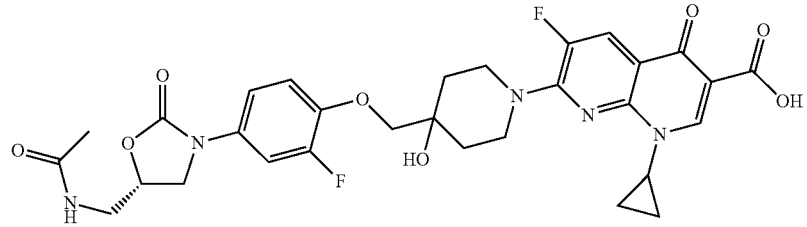 [SMILES: CC(=O)NC[C@H]1CN(c2ccc(OCC3(O)CCN(c4nc5c(cc4F)c(=O)c(C(=O)O)cn5C4CC4)CC3)c(F)c2)C(=O)O1]

Step 1: (4-Benzyloxy-3-fluoro-phenyl)-carbamic acid benzyl ester

A solution of 34.9 g 1-benzyloxy-2-fluoro-4-nitro-benzene (WO03064413) (MW: 247.28, 141 mmol) and 340 mg platine 5% on activated carbon in 350 ml ethyl acetate was stirred under hydrogen at rt and normal pressure. The reaction was monitored by HPLC and was complete after twenty hours. The catalyst was filtered over a glass fibre filter, and the filtrate evaporated under reduced pressure to dryness. The oily residue was dissolved in 500 ml acetone and treated with 250 ml of a saturated solution of sodium bicarbonate and 17.5 g of sodium bicarbonate (MW: 84.01, 208 mmol). The mixture was cooled to 5° C. and treated drop wise with 26.08 g of benzyl chloroformate (MW: 170.59, 152 mmol). The reaction was allowed to stirred at room temperature for two hours and monitored by TLC (hexane/ethyl acetate 3:1). The acetone was evaporated, the residue diluted with 500 ml water, and the solid filtered off. The crystals were washed with 500 ml water and dried. Yield: 48.05 g, 95.8%. MS: 352.5 (M+H)$^+$, 350.8, (M−H)$^−$. Method ESI$^+$, ESI$^−$.

Step 2: (5R)-3-(4-benzyloxy-3-fluoro-phenyl)-5-hydroxymethyl-oxazolidin-2-one A stirred solution of 17.5 g (4-benzyloxy-3-fluoro-phenyl)-carbamic acid benzyl ester (MW: 351.38, 50 mmol) in 30 ml of dry tetrahydrofurane was cooled to −78° C. with a dry ice/acetone bath. 22.8 ml of a 2.3M n-butyl-lithium solution in n-hexane (52.5 mmol) was added drop wise and the reaction mixture stirred at −78° C. for 15 min. 7.92 g R(−)-glycidyl butyrate (MW: 144.17, 60 mmol) were added and the reaction was allowed to warm up to room temperature. The reaction was monitored by HPLC, quenched with a saturated ammonium chloride solution and diluted with 100 ml of ethyl acetate. The organic layer was washed with 200 ml water and 200 ml brine. The organic layer was dried over magnesium sulfate, filtered and the filtrate evaporated under reduced pressure. The residue was crystallized from 200 ml of a 1/1-ethyl acetate/hexane mixture. The solid was collected and recrystallized from 150 ml of a 9/1 ethyl acetate/dichloromethane mixture. The colorless crystals were collected and dried. Yield: 10.4-g, 65.5%. MS: 318.1 (M+H)$^+$. Method ESI$^+$.

Step 3: (5S)-5-azidomethyl-3-(4-benzyloxy-3-fluoro-phenyl)-oxazolidin-2-one

A solution of 10 g (5R)-3-(4-benzyloxy-3-fluoro-phenyl)-5-hydroxymethyl-oxazolidin-2-one (MW: 317.32, 31.51 mmol) and 4.78 g triethylamine (MW: 101.19, 47.26 mmol) in 300 ml dichloromethane was treated under stirring at 10° C. with 4.32 g of methane sulfonyl chloride (MW: 114.55, 37.82 mmol). The reaction was stirred at room temperature for one hour and monitored by TLC (ethyl acetate:hexane 1:1). The reaction mixture was quenched with 100 ml water and the organic layer washed with 100 ml brine. The organic layer was dried over magnesium sulfate, filtered and the filtrate evaporated under reduced pressure. The residue was dissolved in 100 ml dimethylformamide, 5.12 g sodium azide (MW: 65.01, 78.7 mmol) and a catalytic amount of tetrabutyl ammonium iodide were added. The suspension was stirred at 90° C. over night. The reaction was monitored by HPLC. The dimethylformamide was evaporated under reduced pressure, the residue dissolved in 200 ml dichloromethane and the organic layer washed successively with 100 ml water and 100 ml brine. The dichloromethane solution was dried over magnesium sulfate, filtered, and the filtrate evaporated under reduced pressure.

The residue was crystallized from 150 ml of a 1/1 mixture of ethyl acetate:hexane. The crystals were collected to afford an off white solid. Yield: 10.4-g, 97%. MS: 343.1 (M+H)$^{+-}$. Method: ESI$^+$.

Step 4: N-[(5S)-{3-(3-fluoro-4-hydroxy-phenyl)}-2-oxo-oxazolidin-5-ylmethyl]-acetamide A suspension of 10.4 g (5S)-5-azidomethyl-3-(4-benzyloxy-3-fluorophenyl)oxazolidin-2-one (MW: 342.33, 30.38 mmol) and 1.5 g of palladium 10% on activated carbon in 400 ml of a 1:1 methanol:ethyl acetate mixture was stirred at room temperature under hydrogen for two days. The catalyst was filtered off using a glass fibre filter paper and the filtrate evaporated under reduced pressure. The residue was dissolved in 100 ml of acetic acid, and treated with 3.72 g of acetic anhydride (MW: 102.09, 36.45 mmol). The solvent was evaporated under reduced pressure and the residue crystallized from a 1:1 ethyl acetate:hexane mixture to afford an off white solid. Yield: 6.76-g, 83%. MS: 269.4 (M+H)$^+$, 267.3, (M−H)$^−$. Method ESI$^+$, ESI$^−$.

Step 5: 4-{4-[(5S)-5-(Acetylamino-methyl)-2-oxo-oxazolidin-3-yl]-2-fluoro-phenoxymethyl}-4-hydroxy-piperidine-1-carboxylic acid benzylester A suspension of 22.72 g 1-oxa-6-aza-spiro[2.5]octane-6-carboxylic acid benzyl ester (WO9803507) (MW: 247.29, 92 mmol), 21.45 g N-[(5S)-{3-(3-fluoro-4-hydroxy-phenyl)}-2-oxo-oxazolidin-5-ylmethyl]-acetamide (MW: 268.246, 80 mmol) and 16.58 g potassium carbonate (MW: 138.20, 120 mmol) in 150 ml dimethylformamide was stirred at 100° C. for 7 hours. The reaction was monitored by TLC (dichloromethane/methanol 9:1). The dimethylformamide was evaporated under reduced pressure and the residue was dissolved in 600 ml of a 9:1 dichloromethane/methanol mixture. The organic layer was washed with 400 ml water and 400 ml brine. The organic layer was dried over magnesium sulfate, filtered, and the filtrate diluted with 250 ml ethyl acetate. The mixture was concentrated under reduced pressure to a final volume of 400 ml. The slurry was stirred at room temperature over night. The crystals were filtered and washed successively with 150 ml ethyl acetate and 100 ml pentane. Yield: 31.65 g, 76.7%. MS: 516.8 (M+H)$^+$, Method ESI$^+$.

Step 6: N-[{(5S)-3[3-fluoro-4-(4-hydroxy-piperidin-4-yl-methoxy)-phenyl]-2-oxo-oxazolidin-5-ylmethyl}]-acetamide A suspension of 31 g 4-{4-[(5S)-5-(acetylamino-methyl)-2-oxo-oxazolidin-3-yl]-2-fluorophenoxymethyl}-4-hydroxy-piperidine-1-carboxylic acid benzylester (MW: 515, 54 60.13 mmol) and 2.5 g of palladium 10% on activated carbon in 310 ml methanol and 150 ml ethyl acetate was stirred under hydrogen for 4 hrs. The reaction was monitored by TLC (ethyl acetate). The reaction slurry was diluted with 300 ml methanol, warmed to 40° C., and the catalyst filtered off using a glass fibre filter paper. The filtrate was concentrated to 150 ml, diluted with 300 ml ethyl acetate and concentrated again to 200 ml. 200 ml of diethyl ether were added, and the suspension was cooled to 0° C. under stirring. The solid was collected and dried. Yield: 21.6-g, 94.3%. MS: 382.6 (M+H)$^+$, Method ESI$^+$.

Step 7: 7-(4-{[(5S)-5-(Acetylamino-methyl)-2-oxo-oxazolidin-3-yl]-2-fluoro-phenoxymethyl}-4-hydroxy-piperidin-1-yl)-1-cyclo-propyl-6-fluoro-4-oxo-1,4-dihydro-[1,8]naphthyridine-3-carboxylic acid A suspension of 71 mg 7-chloro-1-cyclopropyl-6-fluoro-1,4-dihydro-4-oxo-[1,8]naphthyridine-3-carboxylic acid (MW: 282.66, 0.25 mmol), 95 mg N-[{(5S)-3-[3-fluoro-4-(4-hydroxy-piperidin-4-ylmethoxy)-phenyl]-2-oxo-oxazolidin-5-ylmethyl}]-acetamide (MW: 381.40, 0.25 mmol) 102 mg triethylamine (MW: 101.19, 1.0 mmol) and 81 mg trimethylchlorsilan (MW: 108.64, 0.75 mmol) in 1 ml N-methyl-pyrrolidin-2-one was heated at 80° C. under stirring for 5 hours. The reaction was monitored by TLC (dichloromethane:methanol 9:1). The N-methyl-pyrrolidin-2-one was evaporated, the residue dissolved in 20 ml of a 9:1 dichloromethane:methanol mixture, and the solution washed sequentially with 10 ml of 0.1 N aqueous hydrochloric acid and 20 ml brine. The organic layer was dried over magnesium sulfate, filtered and the filtrate evaporated. The residue was dissolved in 10 ml of a 9:1 dichloromethane:methanol mixture and diluted with 20 ml ethyl acetate. The precipitated solid was collected to afford an off white solid. A second crop is obtained by concentration under reduced pressure of the mother liquor. Yield: 100 mg, 64%. MS: 628.8 (M+H)$^+$, 626.8 (M−H)$^−$ Method ESI$^+$, ESI$^−$.

Example 73

7-(4-{4-[(5S)-5-(Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-[1,8]naphthyridine-3-carboxylic acid

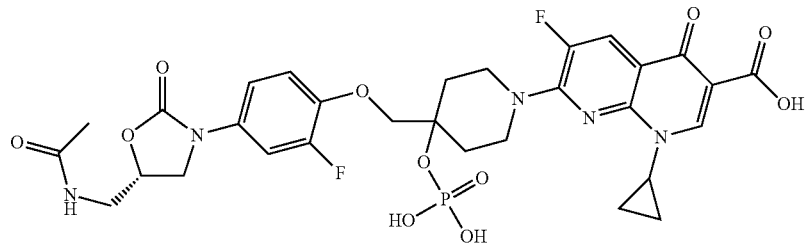 [SMILES: CC(=O)NC[C@H]1CN(c2ccc(OCC3(OP(=O)(O)O)CCN(c4nc5c(cc4F)c(=O)c(C(=O)O)cn5C4CC4)CC3)c(F)c2)C(=O)O1]

Step 1: 7-[4-{4-[(5S)-5-(Acetylamino-methyl)-2-oxo-oxazolidin-3-yl]-2-fluoro-phenoxymethyl}-4-(bis-benzyloxy-phosphoryloxy)-piperidin-1-yl]-1-cyclopropyl-6-fluoro-4-oxo-1,4-dihydro-[1,8]naphthyridine-3-carboxylic acid A suspension of 125 mg 7-(4-{[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-[1,8]naphthyridine-3-carboxylic acid (MW: 627.60, 0.2 mmol) and 42 mg tetrazole (MW: 70.05, 0.6 mmol) in 1 ml dichloromethane was treated with 138 mg of dibenzyl N,N-diisopropylphosphoramidite (MW: 345.42, 0.4 mmol). The original suspension slowly cleared. The solution was stirred at room temperature for two hours and monitored by TLC. (dichloromethane/methanol 9:1). The reaction mixture was cooled to 0° C. and treated with a 0.6 ml of a 0.5M m-chloroperbenzoic acid solution in dichloromethane. The mixture was stirred for two hours at room temperature and diluted with 20 ml dichloromethane. The organic layer was washed successively with 20 ml of a saturated aqueous sodium bicarbonate solution and 20 ml of brine and dried over magnesium sulfate. The slurry was filtered and the filtrate evaporated under reduced pressure. The residue was purified by chromatography over silica using a 9/1 dichloro-methane/methanol mixture as eluent to afford an off white solid. Yield: 158 mg, 89%. MS: 889.3 (M+H)$^+$, 887.0 (M−H)$^−$ Method ESI$^+$, ESI$^−$.

Step 2: 7-(4-{4-[(5S)-(5-Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-[1,8]naphthyridine-3-carboxylic acid A suspension of 158 mg 7-[4-{4-[(5S)-5-(Acetylamino-methyl)-2-oxo-oxazolidin-3-yl]-2-fluoro-phenoxymethyl}-4-(bis-benzyloxy-phosphoryloxy)-piperidin-1-yl]-1-cyclopropyl-6-fluoro-4-oxo-1,4-dihydro-[1,8]naphthyridine-3-carboxylic acid (MW: 887.84, 0.177 mmol) and 20 mg of palladium hydroxide 20% on activated carbon in 20 ml of a 6/3/1 dichloromethane/methanol/water mixture was stirred at room temperature under hydrogen for three hours. The catalyst was filtered off using a glass fibre filter paper. The solvents were evaporated under reduced pressure and the residue dissolved in 10 ml methanol. The solution was diluted with 20 ml water while a white solid precipitated. The solid was collected and dried. Yield: 85 mg, 68%. MS: 709.0 (M+H)$^+$, 706.5 (M−H) Method ESI$^+$, ESI$^−$.

Example 74

7-[4-{4-[(5S)-5-(Acetylamino-methyl)-2-oxo-oxazolidin-3-yl]-2-fluoro-phenoxymethyl}-4-(2,6-di-amino-hexanoyloxy)-piperidin-1-yl]-1-cyclopropyl-6-fluoro-4-oxo-1,4-dihydro-[1,8]naphthyridine-3-carboxylic acid

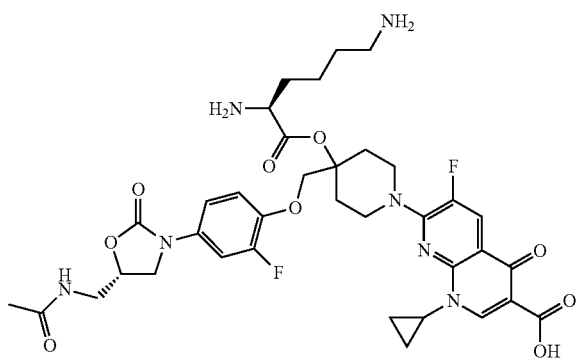 [SMILES: CC(=O)NC[C@H]1CN(c2ccc(OCC3(OC(=O)[C@@H](N)CCCCN)CCN(c4nc5c(cc4F)c(=O)c(C(=O)O)cn5C4CC4)CC3)c(F)c2)C(=O)O1]

Step 1: 4-{4-[(5S)-(5-Acetylamino-methyl)-2-oxo-oxazolidin-3-yl]-2-fluoro-phenoxymethyl}-4-hydroxy-piperidine-1-carboxylic acid tert-butyl ester In analogy of example 72 step 5 by reacting 3.83 g 1-oxa-6-aza-spiro[2.5]octane-6-carboxylic acid tert-butyl ester (WO0204462) (MW: 213.28 18 mmol), 4.02 g N-[(5S)-{3-(3-fluoro-4-hydroxy-phenyl)}-2-oxo-oxazolidin-5-ylmethyl]-acetamide (MW: 268.246, 15 mmol) and 3.1 g potassium carbonate (MW: 138.20, 22.5 mmol) in 30 ml dimethylformamide. Yield: 4.89-g, 67%. MS: 482.6 (M+H)$^+$, Method ESI$^+$.

Step 2: 4-{4-[(5S)-5-(Acetylamino-methyl)-2-oxo-oxazolidin-3-yl]-2-fluoro-phenoxymethyl}-4-(2,6-bis-benzyloxycarbonylamino-hexanoyloxy)-piperidine-1-carboxylic acid tert-butyl ester A suspension of 96 mg of 4-{4-[5-(5S)-(acetylamino-methyl)-2-oxo-oxazolidin-3-yl]-2-fluoro-phenoxymethyl}-4-hydroxy-piperidine-1-carboxylic acid tert-butyl ester (MW: 481.52, 0.2 mmol), 195 mg of Z-Lys (Z)—OH (MW: 414.46, 0.4 mmol) and 49 mg of 4-dimethylaminopyridine (MW: 122.17, 0.4 mmol) in 2 ml dichloromethane was treated under stirring at room temperature with 115 mg N-(3-dimethylaminopropyl)-N'-ethyl-carbodiimide hydrochloride (MW: 191.70, 0.6 mmol). The reaction mixture was stirred over night. The mixture was diluted with 20 ml ethyl acetate and the organic layer washed successively with 10 ml 1 N aqueous hydrochloric acid, 20 ml water and 20 ml brine. The organic layer was dried over magnesium sulfate, filtered and the filtrate evaporated to dryness. The residue was purified by chromatography on silica, using a 9/1 dichloromethane/methanol mixture as eluent to leave a colorless sticky oil. Yield: 150 mg, 88%. MS: 878.8 (M+H)$^+$, Method ESI$^+$.

Step 3: 2,6-Bis-benzyloxycarbonylamino-hexanoic acid 4-{4-[(5S)-5-(acetylamino-methyl)-2-oxo-oxazolidin-3-yl]-2-fluoro-phenoxymethyl}-piperidin-4-yl ester hydrochloride 200 mg of 4-{4-[5-(5S)-(acetylamino-methyl)-2-oxo-oxazolidin-3-yl]-2-fluoro-phenoxymethyl}-4-(2,6-bis-benzyloxycarbonylamino-hexanoyloxy)-piperidine-1-carboxylic acid tert-butyl ester (MW: 977.97, 0.22 mmol) were dissolved in 4 ml of a 1.25M dry hydrochloric acid in methanol. The reaction was stirred at 40° C. for two hours, and the solvent removed by distillation under reduced pressure to leave a off white solid. Yield: 178 mg, quantitative. MS: 778.8 (M+H)$^+$, Method ESI$^+$.

Step 4: 7-[4-{4-[(5S)-5-(Acetylamino-methyl)-2-oxo-oxazolidin-3-yl]-2-fluoro-phenoxymethyl}-4-(2,6-bis-benzyloxycarbonylamino-hexanoyloxy)-piperidin-1-yl]-1-cyclopropyl-6-fluoro-4-oxo-1,4-dihydro-[1,8]naphthyridine-3-carboxylic acid In analogy to example 72 step 7, with 62 mg 7-chloro-1-cyclopropyl-6-fluoro-1,4-dihydro-4-oxo-[1,8]naphthyridine-3-carboxylic acid (MW: 282.66, 0.25 mmol), 178 mg 2,6-bis-benzyl-oxycarbonylamino-hexanoic acid 4-{4-[5-(5S)-(acetylamino-methyl)-2-oxo-oxazolidin-3-yl]-2-fluoro-phenoxymethyl}-piperidin-4-yl ester hydrochloride (MW: 814.31, 0.22 mmol), 90 mg triethylamine (MW: 101.19, 0.88 mmol) and 48 mg trimethylchlorsilan (MW:

108.64, 0.44 mmol) in 1 ml N-methyl-pyrrolidin-2-one. Yield: 94 mg, 42%. MS: 1025.3 (M+H)⁺, Method ESI⁺.

Step 5: 7-[4-{4-[(5S)-5-(Acetylamino-methyl)-2-oxo-oxazolidin-3-yl]-2-fluoro-phenoxymethyl}-4-(2,6-diamino-hexanoyloxy)-piperidin-1-yl]-1-cyclopropyl-6-fluoro-4-oxo-1,4-dihydro-[1,8]naphthyridine-3-carboxylic acid A suspension of 94 mg 7-[4-{4-[(5S)-5-(acetylamino-methyl)-2-oxo-oxazolidin-3-yl]-2-fluoro-phenoxymethyl}-4-(2,6-bis-benzyloxycarbonylamino-hexanoyloxy)-piperidin-1-yl]-1-cyclo-propyl-6-fluoro-4-oxo-1,4-dihydro-[1,8]naphthyridine-3-carboxylic acid (MW: 1024.05, 0.091 mmol) and 20 mg of palladium hydroxide 20% on activated carbon in 20 ml of a 6/3/1 dichloromethane/methanol/water mixture was stirred at room temperature under hydrogen for four hours. The catalyst was filtered off using a glass fibre filter paper. The solvents were evaporated under reduced pressure and the residue dissolved in 10 ml methanol. The solution was diluted with 20 ml water while a white solid precipitated. The solid was collected and dried. Yield: 29 mg, 43%. MS: 757.0 (M+H)⁺, 755.2 Method ESI⁺, ESI⁻.

Example 75

Succinic acid mono-[4-{4-[(5S)-5-(acetylamino-methyl)-2-oxo-oxazolidin-3-yl]-2-fluoro-phenoxymethyl}-1-(6-carboxy-8-cyclopropyl-3-fluoro-5-oxo-5,8-dihydro-[1,8]naphthyridin-2-yl)-piperidin-4-yl] ester

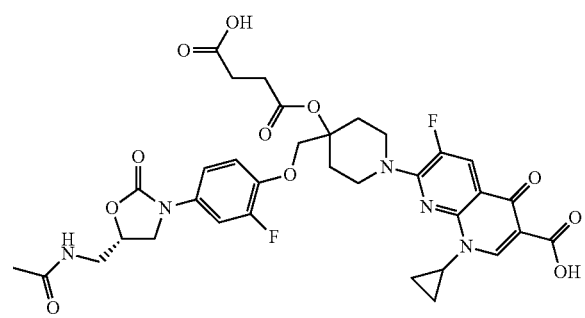 [SMILES: CC(=O)NC[C@H]1CN(c2ccc(OCC3(OC(=O)CCC(=O)O)CCN(c4nc5c(cc4F)c(=O)c(C(=O)O)cn5C4CC4)CC3)c(F)c2)C(=O)O1]

Step 1: Succinic acid 4-{4-[(5S)-5-(acetylamino-methyl)-2-oxo-oxazolidin-3-yl]-2-fluoro-phenoxymethyl}-1-tert-butoxy-carbonyl-piperidin-4-yl ester benzyl ester In analogy of example 74 step 2 with 825 mg 4-{4-[(5S)-5-(acetylamino-methyl)-2-oxo-oxazolidin-3-yl]-2-fluoro-phenoxy-methyl}-4-hydroxy-piperidine-1-carboxylic acid tert-butyl ester (MW: 481.52, 1.71 mmol), 1.07 g of succinic acid mono-benzyl ester (MW: 208.21, 5.14 mmol) and 0.63 g of 4-dimethylaminopyridine (MW: 122.17, 5.1 mmol) in 10 ml dichloromethane was treated under stirring at room temperature with 1.3 g N-(3-dimethylaminopropyl)-N'-ethyl-carbodiimide HCl (MW: 191.70, 6.8 mmol). Yield: 820 mg, 70%. MS: 673.3 (M+H)⁺, Method ESI⁺.

Step 2: Succinic acid 4-{4-[(5S)-5-(acetylamino-methyl)-2-oxo-oxazolidin-3-yl]-2-fluoro-phenoxymethyl}-piperidin-4-yl ester benzyl ester 820 mg of succinic acid 4-{4-[(5S)-5-(acetylamino-methyl)-2-oxo-oxazolidin-3-yl]-2-fluoro-phenoxymethyl}-1-tert-butoxy-carbonyl-piperidin-4-yl ester benzyl ester (MW: 671.72, 1.23 mmol) were dissolved in 4 ml of trifluoro acetic acid. The reaction mixture was stirred at room temperature for one hour. The solvent was evaporated, the residue dissolved in 30 ml of a 9/1 dichloromethane/methanol mixture and the organic layer washed successively with 30 ml of a saturated aqueous sodium bicarbonate solution and 30 ml of brine. The organic layer was dried over magnesium sulfate, filtered and the filtrate evaporated under reduced pressure. The residue was purified by chromatography over silica, using a 95/5 dichloromethane/methanol mixture with 2% triethylamine as eluent. Yield: 420 mg, 60%. MS: 572.7 (M+H)⁺, Method ESI⁺.

Step 3: Succinic acid 4-{4-[(5S)-5-(acetylamino-methyl)-2-oxo-oxazolidin-3-yl]-2-fluoro-phenoxymethyl}-1-(6-carboxy-8-cyclopropyl-3-fluoro-5-oxo-5,8-dihydro-[1,8]naphthyridin-2-yl)-piperidin-4-yl ester benzyl ester In analogy to example 72 step 7, with 113 mg 7-chloro-1-cyclopropyl-6-fluoro-1,4-dihydro-4-oxo-[1,8]naphthyridine-3-carboxylic acid (MW: 282.66, 0.4 mmol), 230 mg succinic acid 4-{4-[(5S)-5-(acetylamino-methyl)-2-oxo-oxazolidin-3-yl]-2-fluoro-phenoxymethyl}-piperidin-4-yl ester benzyl ester (MW: 571.60, 0.4 mmol), 161 mg triethylamine (MW: 101.19, 1.6 mmol) and 87 mg trimethylchlorsilan (MW: 108.64, 0.8 mmol) in 2 ml N-methyl-pyrrolidin-2-one. Yield: 25 mg, 7.6%. MS: 819 (M+H)⁺, 817.8, Method ESI⁺, ESI⁻.

Step 4: Succinic acid mono-[4-{4-[(5S)-5-(acetylamino-methyl)-2-oxo-oxazolidin-3-yl]-2-fluoro-phenoxymethyl}-1-(6-carboxy-8-cyclopropyl-3-fluoro-5-oxo-5,8-dihydro-[1,8]naphthyridin-2-yl)-piperidin-4-yl]ester In analogy to example 74 step 5 with 22 mg succinic acid 4-{4-[(5S)-5-(acetylamino-methyl)-2-oxo-oxazolidin-3-yl]-2-fluoro-phenoxymethyl}-1-(6-carboxy-8-cyclopropyl-3-fluoro-5-oxo-5,8-dihydro-[1,8]naphthyridin-2-yl)-piperidin-4-yl ester benzyl ester (MW: 817.80, 0.026 mmol) and 2 mg of palladium hydroxide 20% on activated carbon in 20 ml of a 1/1 tetrahydrofuran/methanol mixture. Yield: 16 mg, 81%. MS: 729 (M+H)⁺, 727 (M+H)⁻, Method ESI⁺, ESI⁻.

Example 76

7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid

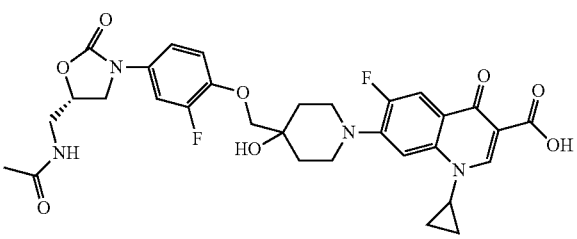 [SMILES: CC(=O)NC[C@H]1CN(c2ccc(OCC3(O)CCN(c4cc5c(cc4F)c(=O)c(C(=O)O)cn5C4CC4)CC3)c(F)c2)C(=O)O1]

A solution of 60 g N-[{(5S)-3[3-fluoro-4-(4-hydroxy-piperidin-4-ylmethoxy)-phenyl]-2-oxo-oxazolidin-5-ylmethyl}]-acetamide. ($C_{18}H_{24}FN_3O_5$, MW: 381.40 0.157 mole) and 26.87 ml of ethyl diisopropylamine (MW: 129.25, 0.157 mole) in 300 ml N-methyl-pyrrolidin-2-one was treated with 67.81 g (7-chloro-1-cyclopropyl-6-fluoro-1,4-dihydro-4-oxo-3-quinolinecarboxylic acid-boron diacetate complex (MW: 410.57, 0.165 mole) and the mixture was stirred at 80° C. for 5 hours. The N-methyl-pyrrolidin-2-one was evaporated under reduced pressure and residue was dissolved in 300 ml of methanol. Anhydrous hydrogen chloride was bubbled through the solution at 10° C. for 30 minutes. The solution was stirred at room temperature while a yellow solid precipitated. The conversion of the boron complex to the free acid was monitored by HPLC. The mixture was diluted with 300 ml ethyl acetate. The solid was filtered and washed with 100 ml of 8/2 ethyl acetate/methanol and 100 ml of ethyl acetate. The yellow solid was dried to leave 86.4 g of a yellow solid. The solid was dissolved in 200 ml dimethylsulfoxyde at 40° C., and the yellow solution was added under stirring to 1000 ml water. The yellow solid was collected, washed with water and dried. Yield: 73 g, 74.5%. MS: 627.8 $(M+H)^+$, 625.8 $(M+H)^-$, Method $ESI^+$, $ESI^-$.

Example 77

7-[4-{4-[(5S)-5-(Acetylamino-methyl)-2-oxo-oxazolidin-3-yl]-2-fluoro-phenoxymethyl}-4-(bis-benzyloxy-phosphoryloxy)-piperidin-1-yl]-1-cyclopropyl-6-fluoro-4-oxo-1,4-dihydro-quinoline-3-carboxylic acid A suspension of 35 g 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid (MW: 626.61, 55.85 mmol) and 6.45 g tetrazole (MW: 70.05, 92.15 mmol) in 700 ml dichloromethane was treated at room temperature under stirring with a solution of 31.8 g dibenzyldiisopropylphosphoramidit (MW: 345.42, 92.15 mmol) in 20 ml dichloromethane. The reaction was monitored by TLC (dichloromethane/methanol 9:1). The reaction was stirred for one hour and the mixture was washed at 0° C. with 200 ml 1N aqueous hydrochloric acid and 100 ml of a saturated sodium bicarbonate solution. The water layer were backwashed with 200 ml dichloromethane. The combined organic layer were concentrated to 500 ml and treated at room temperature with 13.2 ml of a 70% ter-butyl hydroperoxide solution in water (MW: 90.12, 95 mmol). The reaction was stirred for 30 min, diluted with 500 ml dichloromethane and the organic layer washed with 200 ml 1N aqueous hydrochloric acid and with 300 ml brine. The organic layer was dried over magnesium sulfate, filtered and the filtrate evaporated under reduced pressure. The residue was dissolved in 400 ml dichloromethane and diluted with 400 ml N-hexane. The mixture was concentrated (300-mbar, 40° C. bath temperature) to a volume of 400 ml. The sticky oil was decanted and dissolved in 400 ml of refluxing methanol. The solution was concentrated to 300 ml under reduced pressure and stirred over night at RT. The slurry was cooled to 0° C. and the solid collected. Yield: 27.60 g, 55.6%. MS: 888.3 $(M+H)^+$, 885.8 $(M+H)^-$, Method $ESI^+$, $ESI^-$.

Example 78

7-(4-{4-[(5S)-5-(Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid

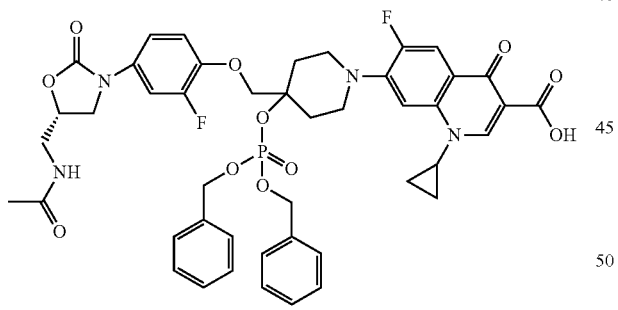

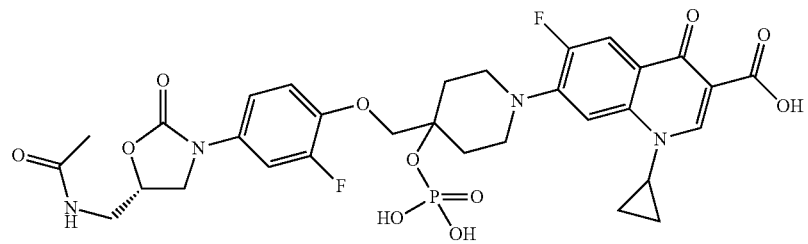 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

27 g 7-[4-{4-[(5S)-5-(acetylamino-methyl)-2-oxo-oxazolidin-3-yl]-2-fluoro-phenoxymethyl}-4-(bis-benzyloxy-phosphoryloxy)-piperidin-1-yl]-1-cyclopropyl-6-fluoro-4-oxo-1,4-dihydro-quinoline-3-carboxylic acid (MW: 886.85, 30.44 mmol) were suspended in 600 ml acetonitrile and treated with 53 ml of a 33% solution of anhydrous hydrobromic acid in acetic acid. The yellow suspension was diluted with 150 ml of acetic acid and was heated to 45° C. The reaction was monitored by HPLC/MS and was complete after 3 hours. The sticky suspension was added to 1.5 L of water under stirring. The off white crystals were collected, washed with 300 ml water, 150 ml ethanol and 150 ml ether. The solid was suspended in 1.3 L water and treated with 35 ml (35 mmol) of a 1M aqueous sodium hydroxide solution. The solid dissolved, and the brown-yellow solution was treated with 15 g of activated charcoal and filtered. The filtrate was extracted with 3 portions of 200 ml of a 95/5 dichloromethane/methanol mixture. The water layer was treated with 40 ml of 1 M HCl solution and the product crystallized by stirring. The solid was collected and dried. Yield: 17.3-g, 80.4%. MS: 609.7 (M+H)$^+$, 607.8 (M+H)$^-$, Method ESI$^+$, ESI$^-$.

Example 79

7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-8-methoxy-4-oxo-1,4-dihydro-quinoline-3-carboxylic acid

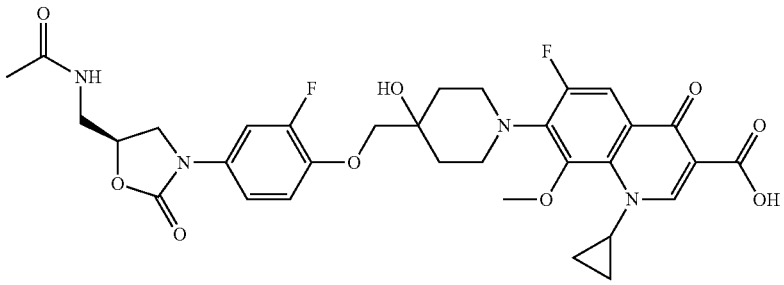 [SMILES: COc1c(N2CCC(O)(COc3ccc(N4C[C@H](CNC(C)=O)OC4=O)cc3F)CC2)c(F)cc2c(=O)c(C(=O)O)cn(C3CC3)c12]

In analogy to example 76 with 114 mg N-[{(5S)-3[3-fluoro-4-(4-hydroxy-piperidin-4-ylmethoxy)-phenyl]-2-oxo-oxazolidin-5-yl-methyl}]-acetamide. (MW: 381.40 0.3 mmol), 127 mg of 1-cyclopropyl-6,7-difluoro-1,4-dihydro-8-methoxy-4-oxo-3-quinolinecarboxylic acid diacetylborate (Sakurai, Nobuhiro; Sano, Mitsuharu; Hirayama, Fumihiro; Kuroda, Tsuyoshi; Uemori, Satoru; Bioorg. Med. Chem. Lett.; 8; 16; 1998; 2185-2190) (MW: 423.137, 0.3 mmol) and 38 mg of ethyl diisopropylamine (MW: 129.25, 0.3 mmol) in 1 ml N-methyl-pyrrolidin-2-one. Yield: 137 mg, 69.5%. MS: 658.2 (M+H)$^+$, 655.8 (M+H)$^-$, Method ESI$^+$, ESI$^-$.

Example 80

7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-8-methoxy-4-oxo-1,4-dihydro-quinoline-3-carboxylic acid

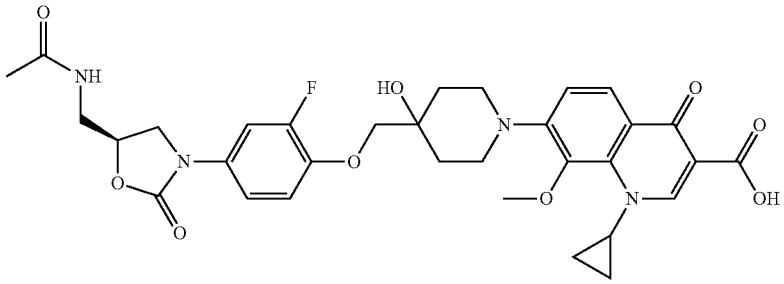 [SMILES: COc1c(N2CCC(O)(COc3ccc(N4C[C@H](CNC(C)=O)OC4=O)cc3F)CC2)ccc2c(=O)c(C(=O)O)cn(C3CC3)c12]

In analogy to example 76 with 114 mg N-[{(5S)-3[3-fluoro-4-(4-hydroxy-piperidin-4-ylmethoxy)-phenyl]-2-oxo-oxazondin-5-yl-methyl}]-acetamide. (MW: 381.40 0.3 mmol), 121 mg of 1-cyclopropyl-8-methoxy-4-oxo-4-di-hydroquinoline-3-carboxylatoboron diacetate (WO03032962) (MW: 405.15, 0.3 mmol) and 77 mg of ethyl diisopropylamine (MW: 129.25, 0.6=1) in 2 ml N-methyl-pyrrolidin-2-one. Yield: 117 mg, 61.2%. MS: 639.8 (M+H)⁺, 637.5 (M+H)⁻, Method ESI⁺, ESI⁻.

Example 81

9-(4-{4-[(5S)-5-(Acetylamino-methyl)-2-oxo-oxazolidin-3-yl]-2-fluoro-phenoxymethyl}-4-hydroxy-piperidin-1-yl)-8-fluoro-3-methyl-6-oxo-2,3-dihydro-6H-1-oxa-3a-aza-phenalene-5-carboxylic acid

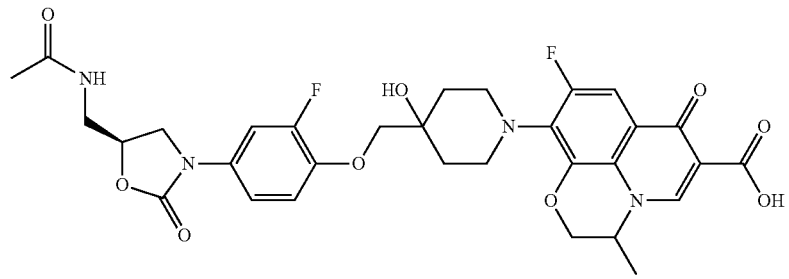 [SMILES: CC(=O)NC[C@H]1CN(c2ccc(OCC3(O)CCN(c4c(F)cc5c(=O)c(C(=O)O)cn6c5c4OCC6C)CC3)c(F)c2)C(=O)O1]

A solution of 140 mg of 9-10-difluoro-2,3-dihydro-3-methyl-7-oxo-7H-pyrido[1,2,3-de]-1,4-benzoxazine-6-carboxilic acid (MW: 281.22, 0.5 mmol), 191 mg of N-[{(5S)-3[3-fluoro-4-(4-hydroxy-piperidin-4-ylmethoxy)-phenyl]-2-oxo-oxazolidin-5-yl-methyl}]-acetamide (MW: 381.40, 0.5 mmol), and 129 mg of ethyl diisopropylamine (MW: 129.25, 1 mmol) was stirred at 80° C. in 1 ml of N-methyl-pyrrolidin-2-one for 24 hours. The solvent was evaporated under reduced pressure. The residue was dissolved in methanol and treated with 10 ml of a 1.2 M anhydrous hydrogen chloride solution in methanol. The methanol was evaporated and the residue digested in ethyl acetate. The solid was collected and crystallized twice from a dichloro-methane/ethanol mixture. Yield: 88 mg, 27%. MS: 643.7 (M+H)⁺, 641.5 (M+H)⁻, Method ESI⁺, ESI⁻.

Example 82

7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-4-oxo-1,4-dihydro-[1,8]naphthyridine-3-carboxylic acid

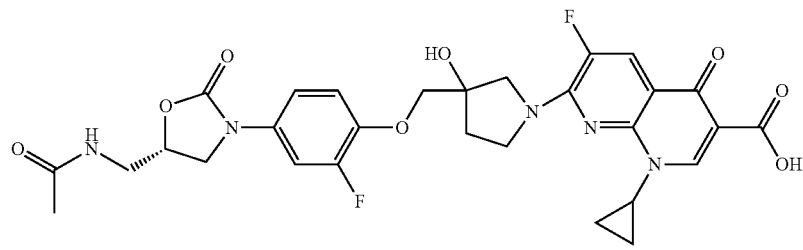 [SMILES: CC(=O)NC[C@H]1CN(c2ccc(OCC3(O)CCN(c4nc5c(cc4F)c(=O)c(C(=O)O)cn5C4CC4)C3)c(F)c2)C(=O)O1]

Step 1: 1-Oxa-5-aza-spiro[2.4]heptane-5-carboxylic acid benzyl ester

A solution 3-methylen-pyrrolidine-1-carboxylic acid benzyl ester (WO9624593) in 5 ml of dichloromethane was treated with 2.16 g sodium bicarbonate (MW: 84.01 26.28 mmol) and 2.47 g of 80% m-chlor-perbenzoic acid (MW: 172.57, 11.48 mmol). The reaction mixture was stirred at room temperature for three hours. The reaction mixture was diluted with 20 ml of a saturated aqueous sodium sulfite solution and 45 ml of dichloromethane. The organic layer was successively washed with 30 ml of an aqueous saturated sodium bicarbonate solution and brine. The organic layer was dried over magnesium sulfate. The residue was purified by chromatography on silica (1/1 ethyl acetate/n-hexane) to afford a off white solid. Yield: 440 mg, 57%. MS: 234.1 (M+H)⁺, Method ESI⁺.

Step 2: 3-{4-[(5S)-5-(Acetylamino-methyl)-2-oxo-oxazolidin-3-yl]-2-fluoro-phenoxymethyl}-3-hydroxy-pyrrolidine-1-carboxylic acid benzyl ester A solution of 420 mg of N-[(5S)-{3-(3-fluoro-4-hydroxy-phenyl)}-2-oxo-oxazolidin-5-ylmethyl]-acetamide (MW: 268.246, 1.56 mmol) in 2 ml dimethylformamide was treated with 83 mg sodium hydride. The suspension was stirred for one hour at room temperature. A solution of 440 mg 1-oxa-5-aza-spiro[2.4]-heptane-5-carboxylic acid benzyl ester (MW: 233.26, 1.88 mmol) in 1 ml DMF was added and the mixture was stirred at 70° C. for three hours. The dimethylformamide was evaporated under reduced pressure and the residue was purified by chromatography over silica (95/5 dichloromethane/methanol mixture with 1% ammonia) to afford an off white powder. Yield: 630 mg, 80%. MS: 502.5 (M+H)⁺, Method ESI⁺.

Step 3: N-{(5S)-3-[3-Fluoro-4-(3-hydroxy-pyrrolidin-3-yl-methoxy)-phenyl}-2-oxo-oxazolidin-5-ylmethyl]-acetamide A suspension of 660 mg 3-{4-[(5S)-5-(acetylamino-methyl)-2-oxo-oxazolidin-3-yl]-2-fluoro-phenoxymethyl}-3-hydroxy-pyrrolidine-1-carboxylic acid benzyl ester (MW: 501.51, 1.31 mmol) and 20 mg palladium 10% on activated carbon in 20 ml of a 1/1 ethyl acetate/methanol mixture was stirred for twelve hours under hydrogen. The catalyst was filtered on a glass fiber filter paper and the filtrate evaporated under reduced pressure to afford a colorless oil. Yield: 400 mg, 83.2%. MS: 368.4 (M+H)$^+$, Method ESI$^+$.

Step 4: 7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-4-oxo-1,4-dihydro-[1,8]naphthyridine-3-carboxylic acid In analogy to example 72, step 7 with 39 mg 7-chloro-1-cyclo-propyl-6-fluoro-1,4-dihydro-4-oxo-[1,8]naphthyridine-3-carboxylic acid (MW: 282.66, 0.24 mmol), 99 mg N-{(5S)-3-[3-fluoro-4-(3-hydroxy-pyrrolidin-3-yl-methoxy)-phenyl}-2-oxo-oxazolidin-5-ylmethyl]-acetamide. (MW: 367.38, 0.24 mmol) 101 mg triethylamine (MW: 101.19, 1.0 mmol) and 80 mg trimethylchlorsilan (MW: 108.64, 0.75 mmol) in 2 ml N-methyl-pyrrolidin-2-one. Yield: 70 mg, 46%. MS: 614.7 (M+H)$^+$, 612.7 (M+H)$^-$, Method ESI$^+$, ESI$^-$.

Example 83

7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-4-oxo-1,4-dihydro-quinoline-3-carboxylic acid

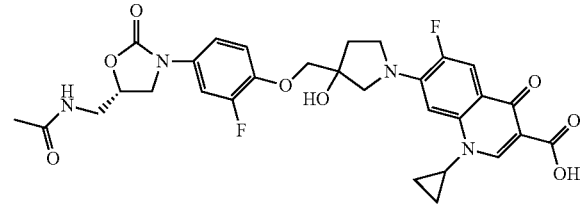 [SMILES: CC(=O)NC[C@H]1CN(c2ccc(OCC3(O)CCN(c4cc5c(cc4F)c(=O)c(C(=O)O)cn5C4CC4)C3)c(F)c2)C(=O)O1]

In analogy to example 76 with 106 mg N-{(5S)-3-[3-fluoro-4-(3-hydroxypyrrolidin-3-ylmethoxy)-phenyl]-2-oxo-oxazolidin-5-yl-methyl}-acetamide. (MW: 367.38, 0.29 mmol) 119 mg (7-chloro-1-cyclopropyl-6-fluoro-1,4-dihydro-4-oxo-3-quinolinecarboxylic acid-boron diacetate complex (MW: 410.57, 0.29 mmol) and 75 mg of ethyl diisopropylamine (MW: 129.25, 0.58 mmol) in 2 ml N-methyl-pyrrolidin-2-one. Yield: 19 mg, 11%. MS: 613.5 (M+H)$^+$, 611.5 (M+H)$^-$, Method ESI$^+$, ESI$^-$.

Example 84

7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-6-fluoro-8-methoxy-4-oxo-1,4-dihydro-quinoline-3-carboxylic acid

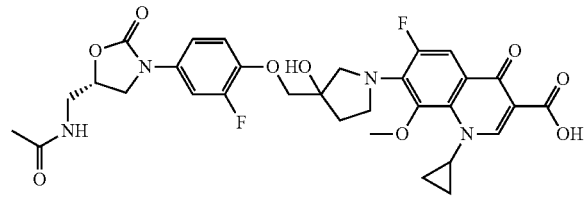 [SMILES: COc1c(N2CCC(O)(COc3ccc(N4C[C@H](CNC(C)=O)OC4=O)cc3F)C2)c(F)cc2c(=O)c(C(=O)O)cn(C3CC3)c12]

In analogy to example 76 with 143 mg N-{(5S)-3-[3-fluoro-4-(3-hydroxy-pyrrolidin-3-ylmethoxy)-phenyl]-2-oxo-oxazolidin-5-yl-methyl}-acetamide (MW: 367.38, 0.39 mmol), 165 mg of 1-cyclo-propyl-6,7-difluoro-1,4-dihydro-8-methoxy-4-oxo-3-quinoline-carboxylic acid diacetylborate (MW: 423.137, 0.39 mmol) and 100 mg of ethyl diisopropylamine (MW: 129.25, 0.78 mmol) in 2 ml N-methyl-pyrrolidin-2-one. Yield: 143 mg, 57%. MS: 643.7 (M+H)$^+$, 641.7 (M+H)$^-$, Method ESI$^+$, ESI$^-$.

Example 85

7-(3-{4-[(5S)-5-(Acetylamino-methyl)-2-oxo-oxazolidin-3-yl]-2-fluoro-phenoxymethyl}-3-hydroxy-pyrrolidin-1-yl)-1-cyclopropyl-8-methoxy-4-oxo-1,4-dihydro-quinoline-3-carboxylic acid

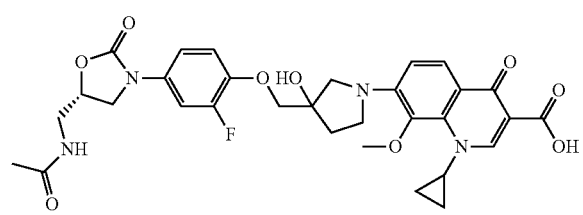 [SMILES: COc1c(N2CCC(O)(COc3ccc(N4C[C@H](CNC(C)=O)OC4=O)cc3F)C2)ccc2c(=O)c(C(=O)O)cn(C3CC3)c12]

In analogy to example 76 with 48 mg N-{(5S)-3-[3-fluoro-4-(3-hydroxy-pyrrolidin-3-ylmethoxy)-phenyl}-2-oxo-oxazolidin-5-yl-methyl]-acetamide (MW: 367.38, 0.13 mmol), 53 mg of 1-cyclo-propyl-8-methoxy-4-oxo-1,4-dihydro-quinoline-3-carboxylatoboron diacetate (MW: 405.15, 0.13 mmol) and 33 mg of ethyl di-isopropylamine (MW: 129.25, 0.26 mmol) in 1 ml N-methyl-pyrrolidin-2-one. Yield: 41 mg, 50%. MS: 625.8 (M+H)$^+$, 623.8 (M+H)$^-$, Method ESI$^+$, ESI$^-$.

Example 86

9-(3-{4-[(5S)-5-(Acetylamino-methyl)-2-oxo-oxazolidin-3-yl]-2-fluoro-phenoxymethyl}-3-hydroxy-pyrrolidin-1-yl)-8-fluoro-3-methyl-6-oxo-2,3-dihydro-6H-1-oxa-3a-aza-phenalene-5-carboxylic acid

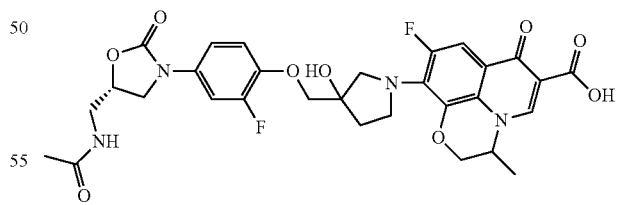

In analogy to example 81 with 110 mg of 9-10-difluoro-2,3-dihydro-3-methyl-7-oxo-7H-pyrido[1,2,3-de]-1,4-benzoxazine-6-carboxylic acid (MW: 281.22, 0.39 mmol), 143 mg of N-{(5S)-3-[3-fluoro-4-(3-hydroxy-pyrrolidin-3-yl-methoxy)-phenyl}-2-oxo-oxazolidin-5-ylmethyl]-acetamide. (MW: 367.38, 0.39 mmol), and 100 mg of ethyl diisopropylamine (MW: 129.25, 0.78 mmol) in 2 ml of N-methyl-pyrrolidin-2-one. Yield: 103 mg, 42%. MS: 629.8 (M+H)$^+$, Method ESI$^+$.

Example 87

7-(4-{4-[(5S)-5-(Acetylamino-methyl)-2-oxo-oxazo-lidin-3-yl]-2-fluoro-phenoxymethyl}-4-hydroxy-azepan-1-yl)-1-cyclopropyl-6-fluoro-4-oxo-1,4-dihydro-quinoline-3-carboxylic acid

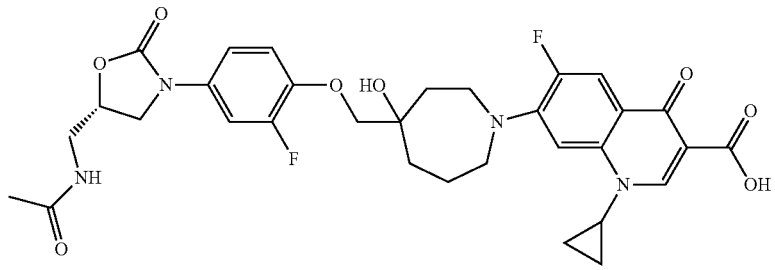 [SMILES: CC(=O)NC[C@H]1CN(c2ccc(OCC3(O)CCCN(c4cc5c(cc4F)c(=O)c(C(=O)O)cn5C4CC4)CC3)c(F)c2)C(=O)O1]

Step 1: 4-Methylene-azepane-1-carboxylic acid tert-butyl ester

A solution of 1 g methyltriphenylphosphoniumbromide (MW: 357.22, 2.79 mmol) in 20 ml of tetrahydrofurane was treated at −78° C. with 1.22 ml of a 2.3 M n-butyl lithium solution in N-hexane (2.8 mmol). The reaction mixture was stirred at −78° C. for ten minutes, then at 0° C. for one hour. The yellow suspension was cooled to −78° C. and treated with a solution of 595 mg 4-oxo-azepane-1-carboxylic acid tert-butyl ester (WO 2000044376) (MW: 213.279, 2.78 mmol) in 10 ml tetrahydrofurane. The reaction mixture was stirred at room temperature for one and half hour. The reaction mixture was quenched with 30 ml of a saturated aqueous solution of ammonium chloride, diluted with 30 ml of ethyl acetate. The organic layer was successively washed with 30 ml water and 30 ml brine, dried over magnesium sulfate and filtered. The filtrate was evaporated under reduced pressure and the residue purified by chromatography over silica. (cyclohexane: ethyl acetate 1:1). Yield: 487 mg, 83%. NMR (CDCl$_3$): 1.35 ppm (s, 9H, tert-but.); 1.6 ppm (m, 2H, —CH$_2$—), 2.14 ppm (m, 2H), 2.33 ppm (m, 2H); 3.29 ppm (m, 4H, N—CH$_2$); 4.67 ppm (m, 2H, vinyl-CH$_2$).

Step 2: 1-Oxa-6-aza-spiro[2.6]nonane-6-carboxylic acid tert-butyl ester

In analogy to example 82 step 1 with 4-methylene-azepane-1-carboxylic acid tert-butyl ester (MW: 211.307, 1.73 mmol), 1.16 g sodium bicarbonate (MW: 84.01 13.8 mmol) and 1.36 g of 80% m-chloroperbenzoic acid (MW172.57, 6.05 mmol) in 5 ml of dichloromethane. Yield: 250 mg, 63%. MS: 228.8 (M+H)$^+$, 127.8 (M-(CH$_3$)$_3$COCO) method ESI$^+$.

Step 3: 4-{4-[(5S)-5-(Acetylamino-methyl)-2-oxo-oxazolidin-3-yl]-2-fluoro-phenoxymethyl}-4-hydroxy-azepane-1-carboxylic acid tert-butyl ester In analogy to example 72 step 5 with 247 mg of 1-oxa-6-aza-spiro[2.6]nonane-6-carboxylic acid tert-butyl ester. (MW: 227.31 1.08 mmol), 296 mg N-[(5S)-{3-(3-fluoro-4-hydroxy-phenyl)}-2-oxo-oxazolidin-5-ylmethyl]-acetamide (MW: 268.246, 80 mmol) and 228 mg potassium carbonate (MW: 138.20, 1.65 mmol) in 150 ml dimethylformamide. Yield: 334 mg, 62%. MS: 496.8 (M+H)$^+$, 440.8 (M-C(CH$_3$)$_3$+H)$^+$, Method ESI$^+$.

Step 4: N-{(5S)-3-[3-Fluoro-4-(4-hydroxy-azepan-4-ylmethoxy)-phenyl]-2-oxo-oxazolidin-5-ylmethyl}-acetamide A solution of 334 mg 4-{4-[(5S)-5-(acetylamino-methyl)-2-oxo-oxazolidin-3-yl]-2-fluoro-phenoxymethyl}-4-hydroxy-azepane-1-carboxylic acid tert-butyl ester (MW: 495.55, 0.674 mmol) in 3 ml of a 1.25 M anhydrous hydrogen chloride solution in methanol was stirred at 35° C. for four hours. The solvent was evaporated under reduced pressure. The residue was dissolved in 4 ml water and the water layer neutralized to pH 7 with a saturated sodium bicarbonate solution. The water was evaporated and the residue dissolved in 30 ml of a 9/1 dichloromethane/methanol mixture. The unsoluble salt were filtered and the filtrate evaporated to dryness to afford off white solid. Yield 266 mg, quant. MS: 395.8 (M+H)$^+$, 440.6 (M+HCOO$^-$), Method ESI$^+$, ESI$^-$.

Step 5: 7-(4-{4-[(5S)-5-(Acetylamino-methyl)-2-oxo-oxazolidin-3-yl]-2-fluoro-phenoxymethyl}-4-hydroxy-azepan-1-yl)-1-cyclo-propyl-6-fluoro-4-oxo-1,4-dihydro-quinoline-3-carboxylic acid In analogy to example 76 with 150 mg N-{(5S)-3-[3-fluoro-4-(4-hydroxy-azepan-4-ylmethoxy)-phenyl]-2-oxo-oxazolidin-5-yl-methyl}-acetamide (MW: 395.43) and 98 mg of ethyl diisopropyl-amine (MW: 129.25, 0.758 mmol), 163 mg (7-chloro-1-cyclopropyl-6-fluoro-1,4-dihydro-4-oxo-3-quinolinecarboxylic acid-boron diacetate complex (MW: 410.57, 0.397 mmol) in 2 ml N-methyl-pyrrolidin-2-one. Yield: 70 mg, 28.8%. MS: 641.7 (M+H)$^+$, method ESI$^+$.

Example 88

7-(4-{4-[(5S)-5-(Acetylamino-methyl)-2-oxo-oxazolidin-3-yl]-2-fluoro-phenoxymethyl}-4-hydroxy-azepan-1-yl)-1-cyclopropyl-6-fluoro-4-oxo-1,4-dihydro-[1,8]naphthyridine-3-carboxylic acid In analogy to example 72 step 7 with 98 mg 7-chloro-1-cyclopropyl-6-fluoro-1,4-dihydro-4-oxo-[1,8]naphthyridine-3-carboxylic acid (MW: 282.66, 0.348 mmol), 138 mg N-{(5S)-3-[3-fluoro-4-(4-hydroxy-azepan-4-ylmethoxy)-phenyl]-2-oxo-oxazolidin-5-ylmethyl}-acetamide (MW: 395.43, 0.348 mmol), 140 mg triethylamine (MW: 101.19, 1.39 mmol) and 113 mg trimethylchlorsilan (MW: 108.64, 1.04 mmol) in 1 ml N-methyl-pyrrolidin-2-one. Yield: 150 mg, 77%. MS: 642.7 (M+H)$^+$, 640.7 (M+H)$^-$, Method ESI$^+$, ESI$^-$.

The compounds that were tested against several strains of B. anthracis showed MIC's below 0.03 µg/ml.

The invention claimed is:

1. A method for treating a bacterial infection in a subject comprising administering to the subject one or more compounds according to Formula (II):

(II)

wherein
L has the following structure

X is CR$^5$ or N;
Y is CR$^6$ or N;
Z is a $C_{1-4}$ alkylene group, a $C_{2-4}$ alkenylene group, a $C_{2-4}$ alkynylene group or a $C_{1-4}$ heteroalkylene group; each of which may be substituted by one or more hydroxy or amino groups;
b is 1, 2 or 3;
c is 1, 2 or 3;
R$^1$ is H, F, Cl, Br, I, OH, NH$_2$, an alkyl group or a heteroalkyl group;

R$^2$ is H, F or Cl;
R$^3$ is an ethyl, a 2-propyl, a C3-C6 cycloalkyl, a phenyl or a pyridyl group, each of which may be substituted by one, two or more fluorine atoms or amino groups;
R$^5$ is H, F, Cl, OH, NH$_2$, an alkyl group or a heteroalkyl group;
R$^3$ and R$^5$ can be linked via an alkylene, an alkenylene or a heteroalkylene group or be a part of a cycloalkylene or heterocycloalkylene group; in such case R$^3$ is not H and R$^5$ is not H, F, OH, NH$_2$ or Cl;
R$^6$ is H, F, Cl or OMe;
R$^7$ is hydrogen, a group of formula PO$_3$R$^9_2$ or SO$_3$R$^{10}$ or a heteroalkyl group carrying at least one OH, NH$_2$, SO$_3$R$^{10}$, PO$_3$R$^9_2$, or COOH group, wherein R$^9$ is H, alkyl, cycloalkyl, aryl, or aralkyl, and wherein R$^{10}$ is H, alkyl, cycloalkyl, aryl, or aralkyl;
R$^8$ is a group of the formula —CH$_2$NHCOMe;
or a pharmacologically acceptable salt, solvate, hydrate or formulation thereof.

2. The method according to claim 1, wherein R$^1$ is H.
3. The method according to claim 1, wherein R$^2$ is H or F.
4. The method according to claim 1, wherein R$^3$ is a cyclopropyl group.
5. The method according to claim 1, wherein R$^3$ and R$^5$ together form a bridge of the formula —O—CH$_2$—N(Me)- or —O—CH$_2$—CH(Me)-.
6. The method according to claim 1, wherein R$^7$ is hydrogen or a group of the formula SO$_3$H, PO$_3$H$_2$PO$_3$(CH$_2$C$_6$H$_5$)$_2$, CH$_2$OPO$_3$H$_2$ or COCH$_2$CH$_2$COOH, or together with the oxygen to which it is bound forms an ester of a naturally occurring amino acid or a derivative thereof.
7. The method according to claim 1, wherein L has the following structure:

8. The method according to claim 1, wherein R$^5$ is H, F, Cl or a methoxy group which may be substituted by one, two or three fluorine atoms.
9. The method according to claim 1, wherein X is CH or N.
10. The method according to claim 1, wherein Y is CH.
11. The method according to claim 1, wherein Z is CH$_2$ or CH$_2$CH$_2$.

12. A method for treating a bacterial infection in a subject comprising administering to the subject one or more compounds according to Formula III:

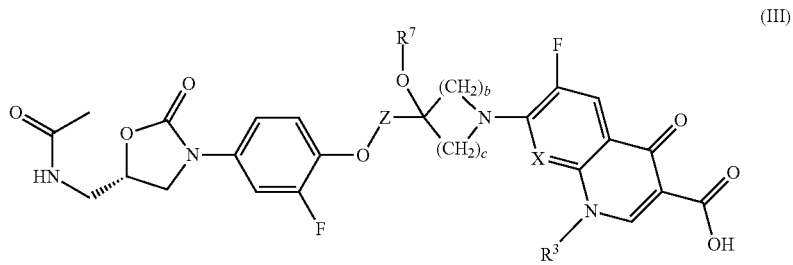

wherein
Z is $CH_2$ or $CH_2CH_2$;
X is CH, N or C-OMe and $R^3$ is cyclopropyl; or
X is $CR^5$ and $R^5$ and $R^3$ together form a bridge of the formula —O—$CH_2$—CH(Me)—;
b is 1, 2 or 3
c is 1, 2 or 3; and
$R^7$ is hydrogen, a group of formula $PO_3R^9{}_2$ or $SO_3R^{10}$ or a heteroalkyl group carrying at least one OH, $NH_2$, $SO_3R^{10}$, $PO_3R^9{}_2$, or COOH group, wherein $R^9$ is H, alkyl, cycloalkyl, aryl, or aralkyl, and wherein $R^{10}$ is H, alkyl, cycloalkyl, aryl, or aralkyl;

or a pharmacologically acceptable salt, solvate, hydrate or formulation thereof.

13. The method according to claim 12, wherein $R^7$ is hydrogen or a group of the formula $SO_3H$, $PO_3H_2$, $PO_3(CH_2C_6H_5)_2$, $CH_2OPO_3H_2$ or $COCH_2CH_2COOH$, or together with the oxygen to which it is bound forms an ester of a naturally occurring amino acid or a derivative thereof.

14. The method according to claim 1 wherein the bacterial infection is a Gram positive bacterial infection.

15. The method according to claim 12 wherein the bacterial infection is a Gram positive bacterial infection.

* * * * *

UNITED STATES PATENT AND TRADEMARK OFFICE
CERTIFICATE OF CORRECTION

PATENT NO. : 8,513,231 B2
APPLICATION NO. : 13/596700
DATED : August 20, 2013
INVENTOR(S) : Christian Hubschwerlen et al.

It is certified that error appears in the above-identified patent and that said Letters Patent is hereby corrected as shown below:

On the Title page, Item (73), replace the Assignee as follows:

from

Morphochem Aktiengesellschaft fü Kombinatorische Chemie, Munich (DE)

to

Morphochem Aktiengesellschaft für Kombinatorische Chemie, Munich (DE)

In the Claims

At Column 70, claim 6, line 46, replace "$PO_3H_2PO_3$ $(CH_2C_6H_5)_2$"

with "$PO_3H_2$, $PO_3(CH_2C_6H_5)_2$"

Signed and Sealed this
Twenty-sixth Day of November, 2013

Margaret A. Focarino
*Commissioner for Patents of the United States Patent and Trademark Office*